(12) United States Patent
Klunk et al.

(10) Patent No.: US 8,138,360 B2
(45) Date of Patent: Mar. 20, 2012

(54) ISOTOPICALLY-LABELED BENZOFURAN COMPOUNDS AS IMAGING AGENTS FOR AMYLOIDOGENIC PROTEINS

(75) Inventors: William E. Klunk, Pittsburgh, PA (US); Chester A. Mathis, Jr., Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 882 days.

(21) Appl. No.: 12/064,146

(22) PCT Filed: Oct. 10, 2006

(86) PCT No.: PCT/US2006/039412
§ 371 (c)(1),
(2), (4) Date: Mar. 3, 2008

(87) PCT Pub. No.: WO2007/047204
PCT Pub. Date: Apr. 26, 2007

(65) Prior Publication Data
US 2008/0274058 A1    Nov. 6, 2008

Related U.S. Application Data

(60) Provisional application No. 60/724,782, filed on Oct. 11, 2005.

(51) Int. Cl.
*C07D 307/79* (2006.01)
*A61K 31/343* (2006.01)
*G01N 33/53* (2006.01)

(52) U.S. Cl. .......................... 549/469; 514/469; 436/504
(58) Field of Classification Search ................. 549/469; 514/469; 436/504
See application file for complete search history.

(56) References Cited

FOREIGN PATENT DOCUMENTS
WO    WO 03/051859 A    6/2003
WO    WO 2004/100998 A2    11/2004

OTHER PUBLICATIONS

Masahiro Ono et al., "Novel benzofuran derivatives for PET imaging of .beta.-amyloid plaques in Alzheimer's disease brains", Journal of Medicinal Chemistry, 49(9), 2725-2730 Coden: JMCMAR; ISSN: 0022-2623, 2006, XP002419265.
M. Ono et al., "Benzofuran derivates as Abeta-aggregate-specific imaging agents for Alzheimer's disease", Nuclear Medicine and Biology, Elsvier, NY, US, vol. 29, No. 6, Aug. 2002, pp. 633-642, XP004381410.

*Primary Examiner* — Bernard Dentz
(74) *Attorney, Agent, or Firm* — Stephen A. Bent; Foley & Lardner LLP

(57) ABSTRACT

Benzofuran compounds which contain at least one detectable label selected from the group consisting of $^{131}I$, $^{123}I$, $^{124}I$, $^{125}I$, $^{76}Br$, $^{75}Br$, $^{18}F$, $^{19}F$, $^{11}C$, $^{13}C$, $^{14}C$ and $^{3}H$ are provided as amyloid imaging agents for detecting brain amyloid deposits as well as other amyloidogenic peptides associated with systemic or localized amyloidosis. Additionally, the compounds are useful for determining if patients, presenting with clinically confusing cases of dementia or presenting with mild cognitive impairment, have Alzheimer's disease. The compounds are additionally useful as surrogate markers for monitoring the efficacy of anti-amyloidosis therapies.

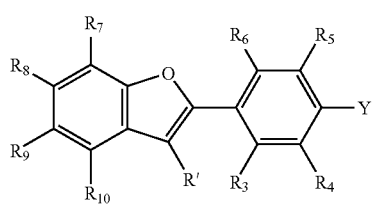

(I)

69 Claims, No Drawings ized benzofuran compounds which are substrates for amyloidogenic proteins, for example, Aβ1-42, an amyloid protein, brain deposits of which are associated with Alzheimer's disease.

ISOTOPICALLY-LABELED BENZOFURAN COMPOUNDS AS IMAGING AGENTS FOR AMYLOIDOGENIC PROTEINS

FIELD OF THE INVENTION

The present invention relates generally to the field of isotopically-labeled benzofuran compounds which are substrates for amyloidogenic proteins, for example, Aβ1-42, an amyloid protein, brain deposits of which are associated with Alzheimer's disease.

BACKGROUND OF THE INVENTION

I. Brain Amyloidosis

Alzheimer's Disease ("AD") is a neurodegenerative illness characterized by memory loss and other cognitive deficits. McKhann et al., *Neurology* 34: 939 (1984). It is the most common cause of dementia in the United States. AD can strike persons as young as 40-50 years of age, yet, because the presence of the disease is difficult to determine without dangerous brain biopsy, the time of onset is unknown. The prevalence of AD increases with age, with estimates of the affected population reaching as high as 40-50% by ages 85-90. Evans et al., *JAMA* 262: 2551 (1989); Katzman, *Neurology* 43: 13 (1993).

Studies suggest that amyloid deposition in the brain is an early, causative event in the pathogenesis of Alzheimer's disease (AD). Progression of amyloid deposition results in the formation of neuritic plaques and neurofibrillary tangles in regions of the brain that are involved with learning and memory. A typical Alzheimer's neuritic plaque comprises dystrophic neurites surrounding a core of amyloid material. The principal component of the amyloid core is a protein called amyloid-beta (Aβ).

In practice, AD is definitively diagnosed through examination of brain tissue, usually at autopsy. Khachaturian, *Arch. Neurol.* 42: 1097 (1985); McKhann et al., *Neurology* 34: 939 (1984). Neuropathologically, this disease is characterized by the presence of neuritic plaques (NP), neurofibrillary tangles (NFT), and neuronal loss, along with a variety of other findings. Mann, *Mech. Ageing Dev.* 31: 213 (1985). Post-mortem slices of brain tissue of victims of Alzheimer's disease exhibit the presence of amyloid in the form of proteinaceous extracellular cores of the neuritic plaques that are characteristic of AD.

The amyloid cores of these neuritic plaques are composed of a protein called the β-amyloid (Aβ) that is arranged in a predominately beta-pleated sheet configuration. Mori et al., *Journal of Biological Chemistry* 267: 17082 (1992); Kirschner et al., *PNAS* 83: 503 (1986). Neuritic plaques are an early and invariant aspect of the disease. Mann et al., *J. Neurol. Sci.* 89: 169; Mann, *Mech. Ageing Dev.* 31: 213 (1985); Terry et al., *J. Neuropathol. Exp. Neurol* 46: 262 (1987).

The initial deposition of Aβ probably occurs long before clinical symptoms are noticeable. The currently recommended "minimum microscopic criteria" for the diagnosis of AD is based on the number of neuritic plaques found in brain. Khachaturian, *Arch. Neurol.* (1985), supra. Assessment of neuritic plaque counts must be delayed until after death, however.

Amyloid-containing neuritic plaques are a prominent feature of selective areas of the brain in AD as well as Down's Syndrome and in persons homozygous for the apolipoprotein E4 allele who are very likely to develop AD. Corder et al., *Science* 261: 921 (1993); Divry, P., *J. Neurol. Psych.* 27: 643-657 (1927); Wisniewski et al., in Zimmerman, H. M. (ed.): PROGRESS IN NEUROPATHOLOGY (Grune and Stratton, N.Y. 1973) pp. 1-26.

Brain amyloid is readily demonstrated by staining brain sections with thioflavin S or Congo red. Puchtler et al., *J. Histochem. Cytochem.* 10: 35 (1962). Congo red-stained amyloid is characterized by a dichroic appearance, exhibiting a yellow-green polarization color. The dichroic binding is the result of the beta-pleated sheet structure of the amyloid proteins. Glenner, G. *N. Eng. J. Med.* 302: 1283 (1980). A detailed discussion of the biochemistry and histochemistry of amyloid can be found in Glenner, *N. Eng. J. Med.,* 302: 1333 (1980).

Thus far, diagnosis of AD has been achieved mostly through clinical criteria evaluation, brain biopsies and post-mortem tissue studies. Research efforts to develop methods for diagnosing Alzheimer's disease in vivo include genetic testing, immunoassay methods, and imaging techniques.

Evidence that abnormalities in Aβ metabolism are necessary and sufficient for the development of AD is based on the discovery of point mutations in the Aβ precursor protein in several rare families with an autosomal dominant form of AD. Hardy, *Nature Genetics* 1: 233 (1992); Hardy et al., *Science* 256: 184 (1992). These mutations occur near the N- and C-terminal cleavage points necessary for the generation of Aβ from its precursor protein. St. George-Hyslop et al., *Science* 235: 885 (1987); Kang et al., *Nature* 325: 733 (1987); Potter WO 92/17152. Genetic analysis of a large number of AD families has demonstrated, however, that AD is genetically heterogeneous. St. George-Hyslop et al., *Nature* 347: 194 (1990). Linkage to chromosome 21 markers is shown in only some families with early-onset AD and in no families with late-onset AD. More recently a gene on chromosome 14 whose product is predicted to contain multiple transmembrane domains and resembles an integral membrane protein has been identified by Sherrington et al., *Nature* 375: 754-760 (1995). This gene may account for up to 70% of early-onset autosomal dominant AD. Preliminary data suggests that this chromosome 14 mutation causes an increase in the production of Aβ. Scheuner et al., *Soc. Neurosci. Abstr.* 21: 1500 (1995). A mutation on a very similar gene has been identified on chromosome 1 in Volga German kindreds with early-onset AD. Levy-Lahad et al., *Science* 269: 973-977 (1995).

Screening for apolipoprotein E genotype has been suggested as an aid in the diagnosis of AD. Scott, *Nature* 366: 502 (1993); Roses, *Ann. Neurol.* 38: 6-14 (1995). Difficulties arise with this technology, however, because the apolipoprotein E4 allele is only a risk factor for AD, not a disease marker. It is absent in many AD patients and present in many non-demented elderly people. Bird, *Ann. Neurol.* 38: 2-4 (1995).

Immunoassay methods have been developed for detecting the presence of neurochemical markers in AD patients and to detect an AD related amyloid protein in cerebral spinal fluid. Warner, *Anal. Chem.* 59: 1203A (1987); World Patent No. 92/17152 by Potter; Glenner et al., U.S. Pat. No. 4,666,829. These methods for diagnosing AD have not been proven to detect AD in all patients, particularly at early stages of the disease and are relatively invasive, requiring a spinal tap. Also, attempts have been made to develop monoclonal antibodies as probes for imaging of Aβ. Majocha et al., *J. Nucl. Med.,* 33: 2184 (1992); Majocha et al., WO 89/06242 and Majocha et al., U.S. Pat. No. 5,231,000. The major disadvantage of antibody probes is the difficulty in getting these large molecules across the blood-brain barrier. Using antibodies for in vivo diagnosis of AD would require marked abnormalities in the blood-brain barrier in order to gain access into the brain. There is no convincing functional evidence that abnormalities in the blood-brain barrier reliably exist in AD. Kalaria, *Cerebrovascular & Brain Metabolism Reviews* 4:226 (1992).

Radiolabeled Aβ peptide has been used to label diffuse, compact and neuritic type plaques in sections of AD brain. See Maggio et al., WO 93/04194. However, these peptides share all of the disadvantages of antibodies. Specifically, peptides do not normally cross the blood-brain barrier in amounts necessary for imaging and because these probes react with diffuse plaques, they may not be specific for AD.

Neuritic plaques and neurofibrillary tangles are the two most characteristic pathological hallmarks of AD. Klunk and Abraham, *Psychiatric Development*, 6:121-152 (1988). Plaques occur earliest in neocortex where they are relatively evenly distributed. Thal et al., *Neurology* 58:1791-1800 (2002). Tangles appear first in limbic areas such as the transentorhinal cortex and progress in a predictable topographic pattern to the neocortex. Braak and Braak, *Acta Neuropathologica* 82:239-259 (1991). Arnold et al. mapped the distribution of NFT and neuritic plaques in the brains of patients with AD. Arnold et al., *Cereb. Cortex* 1:103-116 (1991). Compared to NFT, neuritic plaques were, in general, more evenly distributed throughout the cortex, with the exceptions of notably fewer neuritic plaques in limbic periallocortex and allocortex (the areas with greatest NFT density). By thioflavin-S staining, temporal and occipital lobes had the highest neuritic plaque densities, limbic and frontal lobes had the lowest, and parietal lobe was intermediate. Arriagada et al., *Neurology* 42:1681-1688 (1992). Arriagada et al studied the topographic distribution of AD-type pathologic changes in the brains of presumed nondemented elderly individuals. Their observations suggest that most individuals over the age of 55 have at least a few NFT and plaques. Immunohistochemically defined subtypes of SP had distinct patterns of distribution with Aβ-immunoreactive plaques present in neocortical areas much greater than limbic areas and Alz-50 immunoreactive plaques being infrequent and limited to those areas that contain Alz-50-positive neurons and NFT. These patterns suggested a commonality in the pathologic processes that lead to NFT and SP in both aging and AD.

There remains debate as to whether plaques and tangles are byproducts of the neurodegenerative process found in AD or whether they are the cause of neuronal cell death. Ross, *Current Opinion in Neurobiol.* 96:644-650 (1996); Terry, *J. of Neuropath. & Exp. Neurol.* 55:1023-1025 (1996); Terry, *J Neural Transmission*—Suppl. 53:141-145 (1998). Evidence is clear that neocortical and hippocampal synapse loss correlates well with pre-morbid cognitive status. Some researchers suggest that disruption of microtubule structure and function, caused by the hyperphosphorylation of the microtubule-associated protein, tau, plays the key etiologic role in synapse loss in particular and AD in general. Terry, *J. of Neuropath. & Exp. Neurol.* 55:1023-1025 (1996); Terry, *J of Neural Transmission*—Suppl. 53:141-145 (1998). Oxidative damage and membrane breakdown have been proposed to play important roles in AD. Perry, *Free Radical Biology & Medicine* 28:831-834 (2000); Pettegrew et al., *Annals of the New York Academy of Sciences* 826:282-306 (1997). Vascular factors including subtle, chronic cerebral hypoperfusion also have been implicated in the pathogenesis of AD. De la Torre, *Annals of the New York Academy of Sciences* 903:424-436 (2000); Di Iorio et al., *Aging (Milano)* 11:345-352 (1999). While all of these factors are likely to play some role in the pathogenesis of AD, increasing evidence points to abnormalities in the processing of the amyloid-beta (Aβ) peptide, a 4 kD peptide that aggregates into a fibrillar, β-pleated sheet structure. Glenner and Wong, *Biochemical & Biophysical Research Communications* 120:885-890 (1984). Aβ has been proposed to play an important role in the pathogenesis of AD for several reasons: 1) Aβ deposits are the earliest neuropathological markers of AD in Down's Syndrome, and can precede NFT formation by several decades Mann et al., *Neurodegeneration* 1:201-215 (1992); Naslund, et al., *JAMA* 283:1571-1577 (2000). 2) β-amyloidosis is relatively specific to AD and closely related disorders; Selkoe, *Trends in Neurosciences* 16:403-409 (1993); 3) Aβ is toxic to cultured neurons, Yankner *Neurobiol Aging* 13:615-616 (1992); Mattson et al., *J. Neuroscience* 12:376-389 (1992); Shearman et al., *Proc. Natl. Acad. Sci. USA* 91:1470-1474 (1994), a toxicity that appears to be dependent on β-sheet secondary structure and aggregation into at least oligomers. Lambert et al. *Proc. Natl. Acad. Sci. USA* 95:6448-6453 (1989); Pike et al., *J. Neuroscience* 13:1676-1687 (1993); Simmons et al., *Molecular Pharmacology* 45:373-379 (1994). Although Aβ surely exists in an equilibrium distributed across monomeric, oligomeric and fibrillar/plaque fractions, the oligomeric form of Aβ has been strongly implicated as the key neurotoxic component. Selkoe, *Alzheimer disease*, edited by R. D. Terry, et al, pp. 293-310 Lippincott Williams and Wilkins, Philadelphia (1999); Selkoe, *Science* 298, 789-91 (2002). Recognition of the toxic effects of oligomeric Aβ has formed a basis for compromise for some opponents of the "amyloid cascade hypothesis" of AD. Terry, *Ann. Neurol.* 49:684 (2001). Perhaps the strongest evidence for a role of Aβ in the pathogenesis of AD comes from the finding of mutations in the amyloid precursor protein (APP) gene which lead to some forms of early onset familial AD. Goate et al., *Nature* 349:704-706 (1991). In addition, all familial forms of autosomal dominant AD have in common an elevated level of the more rapidly aggregating 42 amino acid form of Aβ. Younkin *Rinsho Shinkeigaku—Clinical Neurology* 37:1099 (1997). In contrast, no mutation in the tau protein has been shown to cause AD. Instead mutations in tau (chromosome 17) are linked to frontotemporal dementia with Parkinsonism. Goedert et al., *Neuron* 21:955-958 (1998). Recent evidence has shown a good correlation between the levels of Aβ in brain and cognitive decline in AD and the deposition of amyloid appears to be a very early, perhaps the first, event in the pathogenesis of AD, preceding any cognitive impairment. Naslund, et al., *JAMA* 283:1571-1577 (2000). The presence of amyloid deposits may modulate a number of biochemical pathways that result in the deposition of still other proteins, the activation of astroglia and microglia, and eventually neuronal cell death and consequent cognitive dysfunction.

II. Localized and Systemic Amyloidosis

Amyloidosis is a slowly progressive condition, which can lead to significant morbidity and death. A diverse group of disease processes fall under the "amyloidosis" rubric, which is characterized by extracellular tissue deposits, in one or many organs, of various insoluble fibrillar proteins, generically termed "amyloid," in amounts sufficient to impair normal function.

Amyloid deposits are extracellular and not metabolized or cleared by the body. Amyloid may be distinguished grossly by a starch-like staining reaction with iodine; hence the name amyloid. Microscopically, amyloid is differentiated by its extracellular distribution, by its tinctorial and optical properties when stained with Congo red, and by its protein fibril structure. Thus, under light microscopy, amyloid is a homogeneous, highly refractile substance with an affinity for Congo red dye, both in fixed tissues and in vivo. Under electron microscopy, amyloid consists of 100 A° (10 nm), linear nonbranching fibrils; under x-ray diffraction, it has a cross-beta pattern.

The diseases associated with amyloidosis are all typified by an accumulation amyloid deposits. The amyloid deposits are characterized by the presence of one or more amyloidogenic proteins, which are derived from precursor proteins that either have an abnormal structure or are abnormally increased in the serum.

The cause of amyloid production and its deposition in tissues is unknown. In the different biochemical types of amyloidosis, etiologic mechanisms may vary. In secondary amyloidosis, for example, a defect in the metabolism of the precursor protein (the acute-phase reactant: serum amyloid A) may exist, whereas in hereditary amyloidosis a genetically variant protein appears to be present. In primary amyloidosis, a monoclonal population of marrow cells produces fragments of or whole light chains that may be processed abnormally to form amyloid.

Three major types of amyloid and several less common forms have been defined biochemically. The first type, which has an N-terminal sequence that is homologous to a portion of the variable region of an immunoglobulin light chain, is called AL and occurs in primary amyloidosis and in amyloidosis associated with multiple myeloma. The second type has a unique N-terminal sequence of a nonimmunoglobulin protein called AA protein and occurs in patients with secondary amyloidosis. The third type, which is associated with familial amyloid polyneuropathy, is usually a transthyretin (prealbumin) molecule that has a single amino acid substitution. Other hereditary amyloids have been found to consist of mutant gelsolin in some families, mutant apolipoprotein A-I in several others, and other mutant proteins in hereditary cerebral artery amyloid. In the amyloid associated with chronic hemodialysis, 2-microglobulin has constituted amyloid protein. Amyloid associated with aging in skin and with endocrine organs may represent other biochemical forms of amyloidosis. The amyloid found in the histopathologic lesions of Alzheimer's disease consists of proteins. Chemical analyses relating to various forms of amyloidosis have led to a more refined classification. A unique protein, a pentraxin called AP (or serum AP), is universally associated with all forms of amyloid and forms the basis of a diagnostic test.

Three major systemic clinical forms are recognized currently. Amyloidosis is classified as primary or idiopathic (AL form) when there is no associated disease, and secondary, acquired, or reactive (AA form) when associated with chronic diseases, either infectious (tuberculosis, bronchiectasis, osteomyelitis, leprosy) or inflammatory (rheumatoid arthritis, granulomatous ileitis). Amyloid also is associated with multiple myeloma (AL), Hodgkin's disease (AA), other tumors, and familial Mediterranean fever (AA). Amyloidosis may accompany aging. The third major type appears in familial forms unassociated with other disease, often with distinctive types of neuropathy, nephropathy, and cardiopathy.

In primary (AL) amyloidosis, the heart, lung, skin, tongue, thyroid gland, and intestinal tract may be involved. Localized amyloid "tumors" may be found in the respiratory tract or other sites. Parenchymal organs (liver, spleen, kidney) and the vascular system, especially the heart, are involved frequently.

Secondary (AA) amyloidosis shows a predilection for the spleen, liver, kidney, adrenals, and lymph nodes. No organ system is spared, however, and vascular involvement may be widespread, though clinically significant involvement of the heart is rare. The liver and spleen often are enlarged, firm, and rubbery. The kidneys usually are enlarged. Sections of the spleen have large, translucent, waxy areas where the normal malpighian bodies are replaced by pale amyloid, producing the sago spleen.

Hereditary amyloidosis is characterized by a peripheral sensory and motor neuropathy, often autonomic neuropathy, and cardiovascular and renal amyloid. Carpal tunnel syndrome and vitreous abnormalities may occur.

Amyloid associated with certain malignancies (e.g., multiple myeloma) has the same distribution as idiopathic (AL) amyloid; with other malignancies (e.g., medullary carcinoma of the thyroid gland) it may occur only locally in association with the tumor or in metastases. Amyloid frequently is found in the pancreas of individuals with adult-onset diabetes mellitus.

While amyloidosis may be suspected on the basis of specific clinical symptoms and signs, it can be definitively diagnosed only by biopsy. Currently, subcutaneous abdominal fat pad aspiration and biopsy of rectal mucosa are the best screening tests. Other useful biopsy sites are gingiva, skin, nerve, kidney, and liver. Tissue sections should be stained with Congo red dye and observed with a polarizing microscope for the characteristic green birefringence of amyloid. Isotopically labeled serum AP has been used in a scintigraphic test to confirm the diagnosis of amyloidosis. Better diagnostic methodologies need to be developed in order to provide early diagnosis thereby permitting effective treatment.

There is some speculation of a connection between inhibition of amyloid deposits and diabetes therapy, see, e.g., WO 02/16333. Imaging of the pancreas for diagnosing diabetes is one suitable methodology for definitively measuring the levels of amyloid in the pancreas, a correlation of which appears to be indicative of a diagnosis of diabetes.

III. Surrogate Markers

AD is believed to afflict some 4 million Americans and perhaps 20-30 million people worldwide. AD is recognized as a major public health problem in developed nations. Several therapeutic targets have emerged from the ongoing elucidation of the molecular basis of AD. For example, four cholinesterase inhibitors have been approved for the symptomatic treatment of patients with AD-tacrine (Cognex, Warner-Lambert, Morris Plains, N.J.); donepezil (Aricept, Eisai, Inc., Teaneck, N.J., and Pfizer, Inc., New York, N.Y.); rivastigmine (Exelon, Novartis, Basel, Switzerland); and galantamine (Reminyl, Janssen, Titusville, N.J.). Potential new AD therapies that are currently being developed involve immunotherapy, secretase inhibitors or anti-inflammatory drugs. However, to date, there are no available drugs proven to modify the course of cognitive decline.

A major hurdle to developing anti-amyloid therapies is exemplified by the following quote from (Hock, C. et al., 2003, Neuron, 38:547-554), directed to use of immunotherapy as an anti-amyloid therapy: "[w]e do not know whether brain Aβ-amyloid load was reduced in our study patients; in vivo imaging techniques will be required to answer this question." The ability to quantify amyloid load before treatment and then follow the effects of treatment is critical to the efficient development of this class of drugs.

IV. Diagnosing Prodromal Forms of Amyloidosis

A condition closely related to Alzheimer's Disease (AD) is characterized by either isolated memory impairment or impairment in several cognitive domains, but not of sufficient severity to meet diagnostic criteria for Alzheimer's disease.

This condition has been termed mild cognitive impairment (MCI) and may represent a prodromal phase of AD. Mild cognitive impairment is defined as an intermediate or transitional state from a normal cognitive state to dementia. Subjects with a mild cognitive impairment typically have a memory impairment beyond that expected for age and education yet are not demented.

There is some indication that patients diagnosed with mild cognitive impairment will progress to AD. There is also indications that mild cognitive impairment may represent a complex heterogeneous condition and that some patients with mild cognitive impairment will not develop AD or other dementing disorders.

There have been volumes of interest in discerning the boundary of dementia to AD. Most of the interest deals with a boundary or transitional state between normal aging and dementia, or more specifically, Alzheimer disease (AD). Reviews of several studies have indicated that these individuals are at an increased risk for developing AD ranging from 1% to 25% per year. The variability in these rates likely reflects differing diagnostic criteria, measurement instruments, and small sample sizes. See Dawe et al., *Int'l J. Geriatr. Psychiatry* 7: 473 (1992).

Patients diagnosed with an MCI are also becoming of interest for treatment trials. The Alzheimer's Disease Cooperative Study, which is a National Institute on Aging consortium of Alzheimer's Disease research groups, is embarking on a multicenter trial of agents intended to alter the progression of patients with MCI to AD. See Grundman et al., *Neurology*, 1996, A403.

Questions can be raised as to the diagnostic criteria for MCI. Some investigators believe that virtually all these patients with mild disease have AD neuropathologically, and, therefore, this may not be a useful distinction. See Morris et al., *Neurology* 41: 469 (1991). Others note that, while many of these patients progress to AD, not all do and, consequently, that the distinction is an important one. See Grundman, ibid; Petersen et al., *JAMA* 273: 1274 (1995); Petersen et al., *Ann N Y Acad. Sci.* 802: 58 (1996).

V. Substrates for Amyloidogenic Proteins-Radiolabeled Benzofurans

Potential substrates for amyloidogenic proteins have been postulated and range from dye substances, such as Congo Red and derivatives of Chrysamine G (see, e.g., U.S. Pat. No. 6,168,776) to sequence specific peptides that have been labeled for the purpose of imaging insoluble A-beta. These peptides includes the labeled A-beta peptide itself, putrescine-gadolinium-A-beta peptide, radiolabeled A-beta, [$^{111}$In]A-beta, [$^{125}$I]A-beta, A-beta labeled with gamma emitting radioisotopes, A-beta-DTPA derivatives, radiolabeled putrescine, KVLFF-based ligands and derivatives thereof (see, e.g., International Pub. No. WO93/04194 and U.S. Pat. No. 6,331,440).

A few non-radiolabeled benzofurans purported for use in diagnosing Alzheimer's disease were described in U.S. Pat. No. 6,696,039. However, none of the benzofuran compounds disclosed were radiolabeled and none were disclosed to be effective for imaging Alzheimer's disease in a living patient.

Although some labeled benzofurans are known, none have been used in diagnosing Alzheimer's disease. See Aitken et al., *Journal of the Chemical Society, Perkin Transactions 1: Organic and Bio-Organic Chemistry* (1998), (23), 3937-3942 disclosing a deuterated benzofuran derivative; Givens et al. disclose 2-phenyl-benzofuran-d in *Journal of the American Chemical Society* (1993) 115(14), 6001-12 and Davies et al. disclose $^{14}$C labeled 2-phenyl-benzofuran in Journal of the Chemical Society (1959) 3544-7.

A need therefore exists for isotopically-labeled benzofurans having that are capable of crossing the blood brain barrier and binding to insoluble amyloid deposits for imaging in diagnosing Alzheimer's disease.

SUMMARY OF THE INVENTION

The present invention satisfies this need and others by providing, in one embodiment, an amyloid binding compound of Formula (I) or a pharmaceutically acceptable salt thereof:

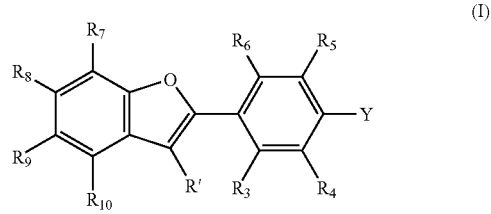

(I)

In formula (I), Y is H, NO$_2$, —NR''$_3^+$, F, Cl, Br, I, —O—(CR''$_2$)$_n$—X, or —(CR''$_2$)$_n$—X, wherein X is F, Cl, Br or I. Variable n is an integer that is selected from 1-5.

R' is H or a lower alkyl group. Too, R'' is H or a lower alkyl group.

R$_3$-R$_{10}$ are independently selected from the group consisting of H, F, Cl, Br, I, C$_1$-C$_5$ alkyl, (CH$_2$)$_{1-3}$—OR$_{11}$, CF$_3$, —(CH$_2$)$_{1-3}$—X, —O—(CH$_2$)$_{1-3}$—X, CN, —CO—R$_{11}$, —N(R$_{11}$)$_2$, —NR''$_3^+$, —NO$_2$, —CO—N(R$_{11}$)$_2$, —O—(CO)—R$_{11}$, OR$_{11}$, SR$_{11}$, COOR$_{11}$, R$_{ph}$, —CR$_{11}$═CR$_{11}$—R$_{ph}$ and —C(R$_{11}$)$_2$—C(R$_{11}$)$_2$—R$_{ph}$. As mentioned above, X is F, Cl, Br or I. R$_{ph}$ is phenyl optionally substituted with one or more substituents selected from the group consisting of F, Cl, Br, I, C$_1$-C$_5$ alkyl, (CH$_2$)$_{1-3}$—O R$_{11}$, CF$_3$, —(CH$_2$)$_{1-3}$—X, —O—(CH$_2$)$_{1-3}$—X, CN, —CO—R$_{11}$, —N(R$_{11}$)$_2$, —CO—N(R$_{11}$)$_2$, —O—(CO)—R$_{11}$, OR$_{11}$, SR$_{11}$, and COOR$_{11}$, wherein each R$_{11}$ is independently H or C$_1$-C$_5$ alkyl, Additionally, substituent Y or R$^3$-R$^{10}$ comprises at least one detectable label selected from the group consisting of $^{131}$I, $^{123}$I, $^{124}$I, $^{125}$I, $^{76}$Br, $^{75}$Br, $^{18}$F, $^{19}$F, $^{11}$C, $^{13}$C, $^{14}$C and $^3$H.

In another embodiment, there is provided a pharmaceutical composition comprising an effective amount of an amyloid binding compound according formula (I) as described above and a pharmaceutically acceptable carrier.

Yet another embodiment is a method for detecting amyloid deposit(s) in vivo. The method comprises (i) administering to a mammal an effective amount of an amyloid binding compound according formula (I), wherein the compound would bind any amyloid deposit(s) in the mammal; and (ii) detecting binding of the compound to amyloid deposit(s) in the mammal.

Additionally, alone or in combination with any other embodiment herein described, the invention encompasses the use of a compound according to formula (I), as herein defined, for detecting amyloid deposits in vivo in a mammal. In a related embodiment, the invention further provides for the use of a compound of formula (I) in the preparation of a medicament for use in the detection of amyloid deposits in vivo in such a subject.

Still another embodiment is a method for detecting amyloid deposit(s) in vitro. The method comprises (i) contacting a bodily tissue with an effective amount of an amyloid binding compound according to formula (I), wherein the compound would bind any amyloid deposit(s) in the tissue; and (ii) detecting binding of the compound to amyloid deposit(s) in the tissue.

Alone or in combination with any other embodiment herein described, another embodiment is the use of a compound according to formula (I), as herein defined, for detecting amyloid deposits in vitro. In another embodiment, the invention provides for the use of a compound of formula (I) in the preparation of a medicament for use in the detection of amyloid deposits in vitro.

An additional embodiment is a method for distinguishing an Alzheimer's diseased brain from a normal brain. The method comprises (i) obtaining tissues from (i) the cerebellum and (ii) another area of the same brain, of a normal mammal and of a mammal suspected of having Alzheimer's disease;

(ii) contacting the tissues with an amyloid binding compound according to claim 1;

(iii) quantifying the amyloid bound to the compound;

(iv) calculating the ratio of (a) the amount of amyloid in the area of the brain other than the cerebellum to (b) the amount of amyloid in the cerebellum; and (v) comparing the ratio for a normal mammal with the ratio for a mammal suspected of having Alzheimer's disease.

In another embodiment, alone or in combination with any other embodiment herein described, the invention provides the use of a compound according to formula (I), as herein defined, for distinguishing an Alzheimer's diseased brain from a normal brain. Another embodiment is the use of a formula (I) compound in the preparation of a medicament for use in distinguishing an Alzheimer's diseased brain from a normal brain.

Yet another embodiment is a method of detecting amyloid deposits in biopsy or post-mortem human or animal tissue. The method comprises the steps of (a) incubating formalin-fixed or fresh-frozen tissue with a solution of an amyloid binding compound of Formula (I) or a pharmaceutically acceptable salt thereof to form a labeled deposit and (b) detecting the labeled deposit.

In another embodiment, alone or in combination with any other embodiment herein described, the invention provides the use of a compound according to formula (I), as herein defined, for detecting amyloid deposits in biopsy or post-mortem human or animal tissue. Another embodiment is the use of a formula (I) compound in the preparation of a medicament for use in detecting amyloid deposits in biopsy or post-mortem human or animal tissue.

In still another embodiment, there is provided a method of quantifying the amount of amyloid in biopsy or post-mortem tissue. The method comprises the steps of:

a) incubating a radiolabeled derivative of an amyloid binding compound of formula (I) or a pharmaceutically acceptable salt thereof with a homogenate of biopsy or post-mortem tissue, wherein at least one of the substituents in the compound is labeled with a radiolabel selected from the group consisting of $^{125}I$, $^{3}H$, and a carbon-containing substituent, wherein at least one carbon is $^{14}C$;

b) separating the tissue-bound from the tissue-unbound radiolabeled derivative of a compound of formula (I), c) quantifying the tissue-bound radiolabeled derivative of a compound of formula (I), and d) converting the units of tissue-bound radiolabeled derivative of a compound of formula (I) to units of micrograms of amyloid per 100 mg of tissue by comparison with a standard.

In another embodiment, alone or in combination with any other embodiment herein described, the invention provides the use of a compound according to formula (I), as herein defined, for quantifying the amount of amyloid in biopsy or post-mortem tissue. Another embodiment is the use of a formula (I) compound in the preparation of a medicament for use in quantifying the amount of amyloid in biopsy or post-mortem tissue.

In another embodiment, there is provided a method of selectively binding an amyloid binding compound of Formula (I) or a pharmaceutically acceptable salt thereof to amyloid plaques but not neurofibrillary tangles in brain tissue which contains both. The method comprises contacting the amyloid plaques in in vitro binding or staining assays with a compound of Formula (I) at a concentration below about 10 nM.

In yet another embodiment, alone or in combination with any other embodiment herein described, the invention provides the use of a compound according to formula (I), as herein defined, for selectively binding an amyloid binding compound of Formula (I) or a pharmaceutically acceptable salt thereof to amyloid plaques but not neurofibrillary tangles in brain tissue which contains both. Another embodiment is the use of a formula (I) compound in the preparation of a medicament for use in selectively binding an amyloid binding compound of Formula (I) or a pharmaceutically acceptable salt thereof to amyloid plaques but not neurofibrillary tangles in brain tissue which contains both.

In yet another embodiment, there is provided a method of selectively binding in vivo an amyloid binding compound of Formula (I) or a pharmaceutically acceptable salt thereof to amyloid plaques but not to neurofibrillary tangles in brain tissue which contains both. The method comprises administering an effective amount of a compound of Formula (I) or a pharmaceutically acceptable salt thereof such that the blood concentration of the administered compound remains below about 10 nM in vivo.

Still another embodiment is an in vivo or in vitro method for detecting in a subject at least one amyloid deposit comprising at least one amyloidogenic protein. The method comprises the steps of:

(a) administering to a subject suffering from a disease associated with amyloidosis, a detectable quantity of a pharmaceutical composition comprising at least one amyloid binding compound of formula I or a pharmaceutically acceptable salt thereof and a pharmaceutically acceptable carrier, and (b) detecting the binding of the compound to an amyloid deposit comprising at least one amyloidogenic protein.

In yet another embodiment, alone or in combination with any other embodiment herein described, the invention provides the use of a compound according to formula (I), as herein defined, for the in vitro or in vivo detection in a subject of at least one amyloid deposit comprising at least one amyloidogenic protein. Another embodiment is the use of a formula (I) compound in the preparation of a medicament for the in vitro or in vivo detection in a subject of at least one amyloid deposit comprising at least one amyloidogenic protein.

In still another embodiment, there is provided a method of identifying a patient as prodromal to a disease associated with amyloid deposition comprising:

(A) administering to the patient, who is presenting with signs of clinical dementia or clinical signs of a mild cognitive impairment, an amyloid binding compound of formula (I) or a pharmaceutically acceptable salt thereof; then (B) imaging said patient to obtain data; and (C) analyzing said data to ascertain amyloid levels in said patient with reference to a normative level, thereby identifying said patient as prodromal to a disease associated with amyloid deposition.

In still another embodiment, alone or in combination with any other embodiment herein described, the invention provides the use of a compound according to formula (I), as herein defined, for identifying a patient as prodromal to a disease associated with amyloid deposition. Another embodiment is the use of a formula (I) compound in the preparation of a medicament for identifying a patient as prodromal to a disease associated with amyloid deposition.

In another embodiment, there is provided a method of determining the efficacy of therapy in the treatment of amyloidosis. The method comprises (A) administering to a patient in need thereof an effective amount of an amyloid binding compound of formula (I) or a pharmaceutically acceptable salt thereof;

(B) imaging said patient; then (C) administering to said patient in need thereof at least one anti-amyloid agent;

(D) subsequently administering to said patient in need thereof an effective amount of a compound of formula (I);

(E) imaging said patient; and (F) comparing levels of amyloid deposition in said patient before treatment with said at least one anti-amyloid agent to levels of amyloid deposition in said patient after treatment with said at least one anti-amyloid agent.

In still another embodiment, alone or in combination with any other embodiment herein described, the invention provides the use of a compound according to formula (I), as herein defined, for determining the efficacy of therapy in the treatment of amyloidosis. Another embodiment is the use of a formula (I) compound in the preparation of a medicament for determining the efficacy of therapy in the treatment of amyloidosis.

DETAILED DESCRIPTION OF THE INVENTION

The present invention exploits the ability of isotopically-labeled benzofuran derivatives to cross the blood brain barrier in vivo and bind to amyloidogenic proteins.

One example of such binding is the ability of the benzofuran compounds to bind to Aβ deposited in neuritic (but not diffuse) plaques, to Aβ deposited in cerebrovascular amyloid, and to the amyloid consisting of the protein deposited in NFT.

Characterization of Specific Binding to Aβ Synthetic Peptide: Affinity, Kinetics, Maximum Binding The characteristics of benzofuran derivative binding were analyzed using synthetic Aβ(1-40) and 2-(4'-[$^3$H]methylamino-phenyl)-benzothiazole ([$^3$H]BTA-1) in phosphate-buffered saline (pH 7.4) as previously described. Klunk et al., *Life Sci.* 69:1471 (2001); Mathis et al., *Bioorg. Med. Chem. Lett.*, 12:295 (2002).

Amino Acid Sequence for Aβ(1-40) is as Follows:

```
1   2   3   4   5   6   7   8   9   10  11  12
Asp Ala Glu Phe Arg His Asp Ser Gly Tyr Glu Val 13  14  15  16  17  18  19  20  21  22  23  24
His His Gln Lys Leu Val Phe Phe Ala Glu Asp Val 25  26  27  28  29  30  31  32  33  34  35  36
Gly Ser Asn Lys Gly Ala Ile Ile Gly Leu Met Val 37  38  39  40
Gly Gly Val Val
```

DEFINITIONS

"Alkyl" refers to a saturated straight or branched chain hydrocarbon radical. Examples include without limitation methyl, ethyl, propyl, iso-propyl, butyl, iso-butyl, tert-butyl, n-pentyl and n-hexyl.

"Alkenyl" refers to an unsaturated straight or branched chain hydrocarbon radical comprising at least one carbon to carbon double bond. Examples include without limitation ethenyl, propenyl, iso-propenyl, butenyl, iso-butenyl, tert-butenyl, n-pentenyl and n-hexenyl.

"Alkynyl" refers to an unsaturated straight or branched chain hydrocarbon radical comprising at least one carbon to carbon triple bond. Examples include without limitation ethynyl, propynyl, iso-propynyl, butynyl, iso-butynyl, tert-butynyl, pentynyl and hexynyl.

"Alkoxy" refers to an alkyl group bonded through an oxygen linkage.

"Lower" used in combination with alkyl, alkenyl, alkynyl or alkoxy refers to $C_1$-$C_8$ moieties.

"Halo" refers to a fluoro, chloro, bromo or iodo radical.

"Radioactive halo" refers to a radioactive halo, i.e. radiofluoro, radiochloro, radiobromo or radioiodo.

"Effective amount" refers to the amount required to produce a desired effect. Examples of an "effective amount" include amounts that enable detecting and imaging of amyloid deposit(s) in vivo or in vitro, that yield acceptable toxicity and bioavailability levels for pharmaceutical use, and/or prevent cell degeneration and toxicity associated with fibril formation.

"Pharmaceutically acceptable carrier" refers to a pharmaceutically acceptable material, composition or vehicle, such as a liquid or solid filler, diluent, excipient or solvent encapsulating material, involved in carrying or transporting the subject compound from one organ, or portion of the body, to another organ or portion of the body. Each carrier is "acceptable" in the sense of being compatible with the other ingredients of the formulation and suitable for use with the patient. Examples of materials that can serve as a pharmaceutically acceptable carrier include without limitation: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations as identified, for example, in REMINGTON'S PHARMACEUTICAL SCIENCES, 15$^{th}$ ed. (Mack Publishing Co., 1975), at pages 1405-1412 and 1461-1487, and THE NATIONAL FORMULARY XIV, 14$^{th}$ ed. (American Pharmaceutical Association, 1975).

"Pharmaceutically acceptable salt" refers to an acid or base salt of the inventive compound, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

"Prodrug" refers to a derivative of the inventive compound that undergoes biotransformation, such as metabolism, before exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compound using conventional methods, such as that described in BURGER'S MEDICINAL CHEMISTRY AND DRUG CHEMISTRY, 5$^{th}$ ed., Vol. 1 (1995), pages 172-178 and 949-982.

The term "parenteral" as used herein includes subcutaneous, intravenous, intraarterial, intramuscular, intraperitoneal, intrathecal, intraventricular, intrasternal, intracranial, and intraosseous injection and infusion techniques.

"Animal" refers to a living organism having sensation and the power of voluntary movement, and which requires for its existence oxygen and organic food. Examples include, without limitation, members of the human, equine, porcine, bovine, murine, canine and feline species. In the case of a human, an "animal" also may be referred to as a "patient."

"Mammal" refers to a warm-blooded vertebrate animal.

A "subject" is a mammal, such as, for example, a human. A specific example is a human suspected of having dementia.

"Treating" refers to:

(i) preventing a disease, disorder or condition from occurring in an animal that may be predisposed to the disease, disorder and/or condition but has not yet been diagnosed as having it;

(ii) inhibiting the disease, disorder or condition, i.e., arresting its development; and/or (iii) relieving the disease, disorder or condition, i.e., causing regression of the disease, disorder and/or condition.

The term "therapy" includes treating and/or preventing disease.

The term "treating" or "treatment" does not necessarily mean total cure. Any alleviation of any undesired symptom or pathological effect of the disease to any extent or the slowing down of the progress of the disease can be considered treatment. Furthermore, treatment may include acts which may worsen the patient's overall feeling of well being or appearance. For example, the administration of chemotherapy in cancer patients which may leave the patients feeling "sicker" is still considered treatment.

The term "preventing" refers to decreasing the probability that an organism contracts or develops a disease associated with amyloid deposition. For example, the term "preventing" refers to reducing the percentage of individuals who develop the disease relative to a control group that does not undergo administration of an anti-amyloid agent.

A "detectable quantity" means that the amount of the detectable compound that is administered is sufficient to enable detection of binding of the compound to amyloid.

An "imaging effective quantity" means that the amount of the detectable compound that is administered is sufficient to enable imaging of binding of the compound to amyloid.

The term "in vivo imaging" refers to any method which permits the detection of a labeled benzofuran compound as described herein.

The term "in vivo or in vitro method for detecting" refers to any method which permits the detection of a labeled thioflavin derivative of formula (I).

The term "baseline" refers to the amount and distribution of a patient's amyloid deposition prior to initiation of the anti-amyloid therapy.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

Amyloid Imaging Agents

The amyloid imaging agent of the present invention is any compound of formula (I) or a pharmaceutically acceptable salt thereof:

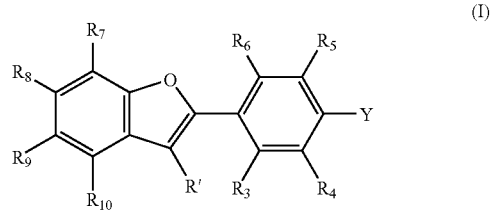

(I)

wherein R', R$_3$-R$_{10}$, and Y are as defined above.

Compounds of formula (I), also referred to herein as "benzofuran compounds," "benzofuran derivatives," or "amyloid imaging agents," have each of the following characteristics: (1) specific binding to synthetic Aβ in vitro, (2) ability to cross a non-compromised blood brain barrier in vivo, (3) specific binding an amyloid deposit which comprises at least one amyloidogenic protein, wherein the amyloidogenic protein is selected from the group consisting of AL, AH, ATTR, Aβ2M, AA, AApoAI, AApoAII, AGel, ALys, AFib, ACys, ABri, ADan, APrP, ACal, AlAPP, AANF, APro, AIns, AMed, AKer, A(tbn), and ALac, (4) bind to Aβ deposited in neuritic (but not diffuse) plaques, to Aβ deposited in cerebrovascular amyloid, and to the amyloid consisting of the protein deposited in NFT and (5) are also non-toxic at appropriate dosage levels and have a satisfactory duration of effect.

In one embodiment, optionally in combination with any other embodiment herein described, Y can be H, NO$_2$, —NR"$_3$$^+$, F, Cl, Br, I, or —(CR"$_2$)$_n$—X.

In one embodiment, R$_3$-R$_{10}$ can be independently selected from the group consisting of H, F, Cl, Br, I, —N(R$_{11}$)$_2$, and OR$_{11}$. In combination with this or any other embodiment herein described, R$_8$ and R$_9$ can be independently OR$_{11}$.

In another embodiment optionally in combination with other embodiments herein described, each of R$_7$ and R$_{10}$ can be H. In yet another embodiment, each of R$_3$, R$_4$, R$_5$, and R$_6$ can be H.

In still other embodiments of the invention, Y can be F, Cl, Br, I, or —NO$_2$. A specific example of Y is F.

In another embodiment, the amyloid binding compound of formula (I) provides for each of R$_3$, R$_4$, R$_5$, and R$_6$, R$_7$, and R$_{10}$ to be H, and R$_8$ and R$_9$ to be independently OR$_{11}$.

Another embodiment provides for Y to comprise at least one detectable label.

Illustrative compounds of formula (I) include but are not limited to:

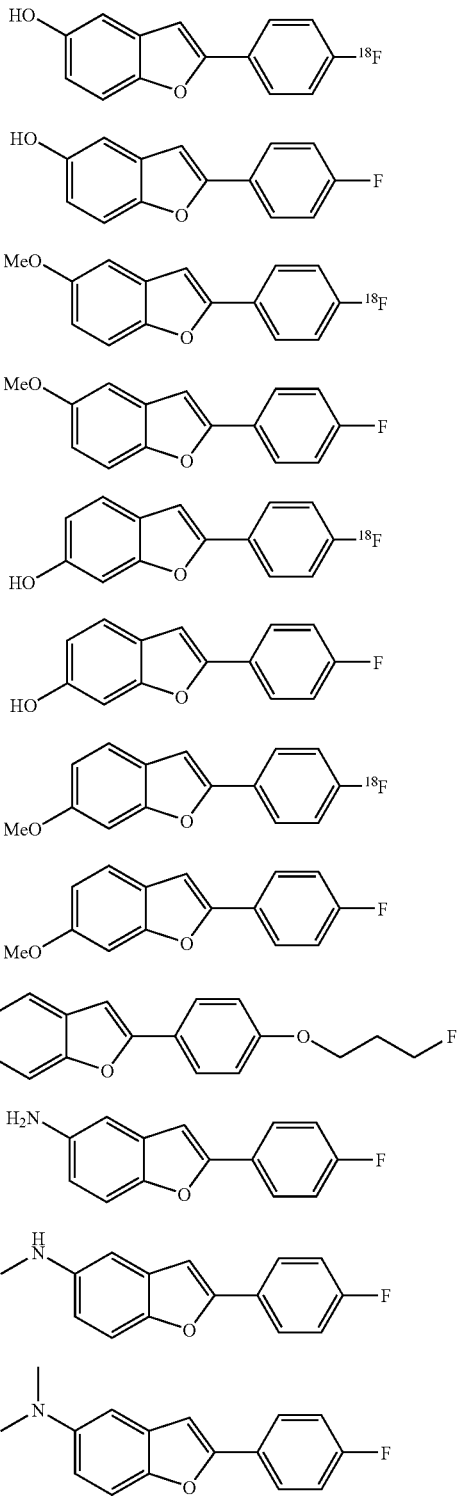

Methods of Use

The inventive compounds may be used to determine the presence, location and/or amount of one or more amyloid deposit(s) in an organ or body area, including the brain, of an animal. Amyloid deposit(s) include, without limitation, deposit(s) of Aβ. In allowing the temporal sequence of amyloid deposition to be followed, the inventive compound may further be used to correlate amyloid deposition with the onset of clinical symptoms associated with a disease, disorder or condition. The inventive compounds may ultimately be used to diagnose a disease, disorder or condition characterized by amyloid deposition, such as AD, familial AD, Down's syndrome, amyloidosis, Type II diabetes mellitus, mild cognitive impairment and homozygotes for the apolipoprotein E4 allele. The inventive compounds also can be used as surrogate markers to assess anti-amyloid therapies.

Imaging Techniques

One method of this invention determines the presence and location of amyloid deposits in an organ or body area, such as the brain, of a patient. The method comprises administration of a detectable quantity of a pharmaceutical composition containing an amyloid binding compound of the present invention called a "detectable compound," or a pharmaceutically acceptable water-soluble salt thereof, to a patient. A "detectable quantity" means that the amount of the detectable compound that is administered is sufficient to enable detection of binding of the compound to amyloid. An "imaging effective quantity" means that the amount of the detectable compound that is administered is sufficient to enable imaging of binding of the compound to amyloid.

The invention employs amyloid imaging agents which, in conjunction with non-invasive neuroimaging techniques such as magnetic resonance spectroscopy (MRS) or imaging (MRI), or gamma imaging such as positron emission tomography (PET) or single-photon emission computed tomography (SPECT), are used to quantify amyloid deposition in vivo. The method involves imaging a patient to establish a baseline of amyloid deposition. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound. The method can further comprise at least one imaging session of a patient following administration of an anti-amyloid therapy. The method can also comprise imaging a patient before and after treatment with at least one anti-amyloid agent. Imaging can be performed at any time during the treatment.

For purposes of in vivo imaging, the type of detection instrument available is a major factor in selecting a given label. For instance, radioactive isotopes and $^{19}F$ can be used for in vivo imaging in the methods of the present invention. The type of instrument used will guide the selection of the radionuclide or stable isotope. For instance, the radionuclide chosen must have a type of decay detectable by a given type of instrument. Another consideration relates to the half-life of the radionuclide. The half-life should be long enough so that it is still detectable at the time of maximum uptake by the target, but short enough so that the host does not sustain deleterious radiation. The radiolabeled compounds of the invention can be detected using gamma imaging wherein emitted gamma irradiation of the appropriate wavelength is detected. Methods of gamma imaging include, but are not limited to, SPECT and PET. In one embodiment, such as for SPECT detection, the chosen radiolabel will lack a particulate emission, but will produce a large number of photons in a 140-200 keV range. For PET detection, the radiolabel will be a positron-emitting radionuclide such as $^{19}$F which will annihilate to form two 511 keV gamma rays that can be detected by the PET camera.

In the present invention, amyloid binding compounds/imaging agents are made which are useful for in vivo imaging and quantification of amyloid deposition. These compounds are to be used in conjunction with non-invasive neuroimaging techniques such as magnetic resonance spectroscopy (MRS) or imaging (MRI), positron emission tomography (PET), and single-photon emission computed tomography (SPECT). In accordance with this invention, the benzofuran compounds may be labeled with $^{19}$F or $^{13}$C for MRS/MRI by general organic chemistry techniques known to the art. For example, see ADVANCED ORGANIC CHEMISTRY: REACTION, MECHANISMS, AND STRUCTURE, 3$^{rd}$ ed. (1985). The benzofuran compounds also may be radiolabeled with $^{18}$F, $^{11}$C, $^{75}$Br, or $^{76}$Br for PET by techniques well known in the art and are described by Fowler, J. and Wolf, A. in POSITRON EMISSION TOMOGRAPHY AND AUTORADIOGRAPHY 391-450 (Raven Press, 1986). The benzofuran compounds also may be radiolabeled with $^{123}$I for SPECT by any of several techniques known to the art. See, e.g., Kulkarni, *Int. J. Rad. Appl. & Inst.* (Part B) 18: 647 (1991). In addition, the benzofuran compounds may be labeled with any suitable radioactive iodine isotope, such as, but not limited to $^{131}$I, $^{125}$I, or $^{123}$I, by iodination of a diazotized amino derivative directly via a diazonium iodide, see Greenbaum, F. *Am. J. Pharm.* 108: 17 (1936), or by conversion of the unstable diazotized amine to the stable triazene, or by conversion of a non-radioactive halogenated precursor to a stable tri-alkyl tin derivative which then can be converted to the iodo compound by several methods well known to the art. See, Satyamurthy and Barrio, *J. Org. Chem.* 48: 4394 (1983), Goodman et al., *J. Org. Chem.* 49: 2322 (1984), and Mathis et al., *J. Labell. Comp. and Radiopharm.* 1994: 905; Chumpradit et al., *J. Med. Chem.* 34: 877 (1991); Zhuang et al., *J. Med. Chem.* 37: 1406 (1994); Chumpradit et al., *J. Med. Chem.* 37: 4245 (1994). For example, a stable triazene or tri-alkyl tin derivative of benzofuran is reacted with a halogenating agent containing $^{131}$I, $^{125}$I, $^{123}$I, $^{76}$Br, $^{75}$Br, $^{18}$F or $^{19}$F. Thus, the stable tri-alkyl tin derivatives of benzofuran are novel precursors useful for the synthesis of many of the radiolabeled compounds within the present invention. As such, these tri-alkyl tin derivatives are contemplated as one embodiment of this invention.

The benzofuran compounds also may be radiolabeled with known metal radiolabels, such as, for example, Technetium-99m ($^{99m}$Tc). Modification of the substituents to introduce ligands that bind such metal ions can be effected without undue experimentation by one of ordinary skill in the radiolabeling art. The metal radiolabeled benzofuran can then be used to detect amyloid deposits. Preparing radiolabeled derivatives of Tc$^{99m}$ is well known in the art. See, for example, Zhuang et al., "Neutral and stereospecific Tc-99m complexes: [99 mTc]N-benzyl-3,4-di-(N-2-mercaptoethyl)-amino-pyrrolidines (P-BAT)" *Nuclear Medicine & Biology* 26(2):217-24, (1999); Oya et al., "Small and neutral Tc(v)O BAT, bisaminoethanethiol (N2S2) complexes for developing new brain imaging agents" *Nuclear Medicine & Biology* 25(2):135-40, (1998); and Hom et al., "Technetium-99m-labeled receptor-specific small-molecule radiopharmaceuticals: recent developments and encouraging results" *Nuclear Medicine & Biology* 24(6):485-98, (1997).

The methods of the present invention can use isotopes that are detectable by nuclear magnetic resonance spectroscopy for purposes of in vivo imaging and spectroscopy. Useful elements in magnetic resonance spectroscopy include but are not limited to $^{19}$F and $^{13}$C.

Suitable radioisotopes for purposes of this invention can be beta-emitters, gamma-emitters, positron-emitters, and x-ray emitters. These radioisotopes include $^{131}$I, $^{123}$I, $^{18}$F, $^{11}$C, $^{75}$Br, and $^{76}$Br. Suitable stable isotopes for use in Magnetic Resonance Imaging (MRI) or Spectroscopy (MRS), according to this invention, include $^{19}$F and $^{13}$C. Suitable radioisotopes for in vitro quantification of amyloid in homogenates of biopsy or post-mortem tissue include $^{125}$I, $^{14}$C, and $^{3}$H. Exemplary radiolabels are $^{11}$C or $^{18}$F for use in PET in vivo imaging, $^{123}$I, for use in SPECT imaging, $^{19}$F for MRS/MRI, and $^{3}$H or $^{14}$C for in vitro studies. However, any conventional method for visualizing diagnostic imaging agents can be utilized in accordance with this invention.

According to one embodiment of the invention which relates to a method of detecting amyloid deposits in biopsy or post-mortem tissue, the method involves incubating formalin-fixed tissue with a solution of a benzofuran amyloid binding compound of the present invention. In one embodiment, the solution is 25-100% ethanol, (with the remainder being water) saturated with a benzofuran amyloid binding compound according to the present invention. Upon incubation, the compound stains or labels the amyloid deposit in the tissue, and the stained or labeled deposit can be detected or visualized by any standard method. Such detection means include microscopic techniques such as bright-field, fluorescence, laser-confocal and cross-polarization microscopy.

The method of quantifying the amount of amyloid in biopsy or post-mortem tissue involves incubating a labeled derivative of benzofuran according to the present invention, or a water-soluble, non-toxic salt thereof, with homogenate of biopsy or post-mortem tissue. The tissue is obtained and homogenized by methods well known in the art. In one embodiment, the label is a radiolabel, although other labels such as enzymes, chemiluminescent and immunofluorescent compounds are well known to skilled artisans. Exemplary radiolabels include but are not limited to $^{125}$I, $^{14}$C and $^{3}$H which are contained in a substituent substituted on one of the compounds of the present formulae described herein. Tissue containing amyloid deposits will bind to the labeled derivatives of the benzofuran amyloid binding compounds of the present invention. The bound tissue is then separated from the unbound tissue by any mechanism known to the skilled artisan, such as filtering. The bound tissue can then be quantified through any means known to the skilled artisan. The units of tissue-bound radiolabeled benzofuran derivative then can be converted to units of micrograms of amyloid per 100 mg of tissue by comparison to a standard curve generated by incubating known amounts of amyloid with the radiolabeled benzofuran derivative.

The method of distinguishing an Alzheimer's diseased brain from a normal brain comprises obtaining tissue from (a) the cerebellum and (b) another area of the same brain, other than the cerebellum, from normal subjects and from subjects suspected of having Alzheimer's disease. Such tissues are made into separate homogenates using methods well known to the skilled artisan, and then are incubated with a radiolabeled benzofuran amyloid binding compound of formula (I). The amount of tissue which binds to the radiolabeled benzofuran amyloid binding compound is then calculated for each tissue type (e.g. cerebellum, non-cerebellum, normal, abnormal) and the ratio for the binding of non-cerebellum to cerebellum tissue is calculated for tissue from normal and for tissue from patients suspected of having Alzheimer's disease. These ratios are then compared. If the ratio from the brain suspected of having Alzheimer's disease is above 90% of the ratios obtained from normal brains, the diagnosis of Alzheimer's disease is made. The normal ratios can be obtained from previously obtained data, or alternatively, can be recalculated at the same time the suspected brain tissue is studied.

The ability of the present compounds to specifically bind to neurofibrially tangles over amyloid plaques is particularly evident at concentrations less than 10 nM, which includes the in vivo concentration range of PET radiotracers. At these low concentrations, which contains only tangles and no plaques, significant binding does not result when compared to control brain tissue containing neither plaques nor tangles. However, incubation of homogenates of brain tissue that contains mainly plaques and some tangles with radiolabeled compounds of the formulae described herein, results in a significant increase in binding when compared to control tissue without plaques or tangles. This data suggests that one advantage of these compounds is their specificity for Aβ deposits at concentrations less than 10 nM. These low concentrations are detectable in PET studies, making PET detection using radiolabeled compounds of the formulae herein described which are specific for Aβ deposits possible. The use of such compounds permits PET detection in Aβ deposits such as those found in plaques and cerebrovascular amyloid. Since it has been reported that Aβ levels in the frontal cortex are increased prior to tangle formation, this would suggest that radiolabeled compounds of the present invention, used as PET tracers, would be specific for the earliest changes in AD cortex. Naslund et al., *JAMA* 283: 1571 (2000).

Method and Use for Detecting Amyloid Deposit(s) In Vivo

As mentioned above, the invention further provides, in one embodiment, a method for detecting amyloid deposit(s) in vivo, comprising:

(i) administering to an animal an effective amount of compound according to formula (I), wherein the compound would bind to any amyloid deposit(s) in the animal; and (ii) detecting binding of the compound to amyloid deposit(s) in the animal.

After a sufficient time has elapsed for the compound to bind with the amyloid deposit(s), for example 30 minutes to 48 hours following administration, the binding may be detected by any means known in the art. Examples of detection means include, without limitation, assays (such as immunometric, calorimetric, densitometric, spectrographic and chromatographic assays), non-invasive neuroimaging techniques (such as magnetic resonance spectroscopy (MRS), magnetic resonance imaging (MRI), and gamma imaging techniques such as single-photon emission computed tomography (SPECT) and positron emission tomography (PET). For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound.

The type of detection instrument available can be a factor in selecting the radioactive halo or carbon isotope. For instance, the selected radioisotope should have a type of decay that is detectable by a given instrument. Another consideration relates to the half-life of the radioisotope. The half-life should be long enough such that the radioisotope is still detectable at the time of maximum uptake by the target, but short enough such that the host does not sustain deleterious radiation. For SPECT detection, the selected radioisotope may lack a particulate emission, but may produce a large number of photons in the 140-200 keV range. For PET detection, the selected radioisotope may be a positron-emitting radioisotope, which annihilates to form two 511 keV gamma rays detectable by a PET camera.

Useful radioisotopes include, without limitation: $^{125}$I, $^{14}$C, and $^{3}$H for in vitro quantification of amyloid in homogenates of biopsy or post-mortem tissue; $^{11}$C and $^{18}$F for PET in vivo imaging; $^{123}$I for SPECT imaging; $^{18}$F for MRS/MRI; $^{3}$H or $^{14}$C for in vitro studies; and $^{18}$F and $^{13}$C for magnetic resonance spectroscopy. In one embodiment, the detecting is effected by gamma imaging, magnetic resonance imaging or magnetic resonance spectroscopy. In another embodiment, the gamma imaging is PET or SPECT.

Method and Use for Detecting Amyloid Deposit(s) In Vitro

This invention further provides a method for detecting amyloid deposit(s) in vitro comprising:

(i) contacting a bodily tissue with an effective amount of a compound according to formula (I), wherein the compound would bind any amyloid deposit(s) in the tissue; and (ii) detecting binding of the compound to amyloid deposit(s) in the tissue.

The binding may be detected by any means known in the art. Examples of detection means include, without limitation, microscopic techniques, such as bright-field, fluorescence, laser-confocal and cross-polarization microscopy.

In one embodiment, the tissue is biopsy or post-mortem tissue that is formalin-fixed or fresh-frozen. In another embodiment, the tissue is homogenized. In yet another embodiment, the inventive compound is in a solution that further comprises 25-99% ethanol, with the remainder of the solution being water. In yet another embodiment, the solution comprises 0-50% ethanol and 0.0001 to 100 μM of the compound. In yet another embodiment, the method further comprises (iii) separating from the tissue the amyloid deposit(s) bound to the compound; and (iv) quantifying the amyloid deposit(s) bound to the inventive compound. The bound amyloid deposit(s) may be separated from the tissue by any means known in the art, such as filtering. The amount of bound amyloid deposit(s) may be converted to units of μg of amyloid deposit(s) per 100 mg of tissue by comparison to a standard curve generated by incubating known amounts of amyloid with the inventive compound or pharmaceutically acceptable salt, hydrate, solvate or prodrug.

Method and Use for Distinguishing Alzheimer's Diseased Brain from Normal Brain

This invention further provides a method for distinguishing an Alzheimer's diseased brain from a normal brain comprising:

(i) obtaining tissues from (a) the cerebellum and (b) another area of the same brain, of a normal animal and of an animal suspected of having Alzheimer's disease;

(ii) contacting the tissues with a compound according to formula (I);

(iii) quantifying the amyloid bound to the compound;

(iv) calculating the ratio of the amount of amyloid in the area of the brain other than the cerebellum to the amount of amyloid in the cerebellum;

(v) comparing the ratio for a normal animal with the ratio for an animal suspected of having Alzheimer's disease.

A diagnosis of Alzheimer's disease may be made if the ratio for an animal suspected of having Alzheimer's disease is, for example, above 90% of the ratio for a normal animal. For this method, a "normal" animal is one that is not suffering from Alzheimer's disease.

Administration and Pharmaceutical Compositions

According to the present invention, a pharmaceutical composition comprising an amyloid imaging agent of formula (I) can be administered to subjects in whom amyloid or amyloid fibril formation are anticipated, e.g., patients clinically diagnosed with Alzheimer's disease or another disease associated with amyloid deposition.

Administration to the subject can be local or systemic and accomplished, for example, intravenously, intraarterially, intrathecally (via the spinal fluid) or the like. Administration also can be intradermal or intracavitary, depending upon the body site under examination. After a sufficient time has elapsed for the compound to bind with the amyloid, for example 30 minutes to 48 hours, the area of the subject under investigation is examined by routine imaging techniques such as MRS/MRI, SPECT, planar scintillation imaging, PET, and any emerging imaging techniques, as well. The exact protocol will necessarily vary depending upon factors specific to the patient, as noted above, and depending upon the body site under examination, method of administration and type of label used; the determination of specific procedures would be routine to the skilled artisan. For brain imaging, as one example, the amount (total or specific binding) of the bound radioactively labeled benzofuran compound or analogue of the present invention is measured and compared (as a ratio) with the amount of labeled benzofuran compound bound to the cerebellum of the patient. This ratio is then compared to the same ratio in age-matched normal brain. For organ imaging, as another example, the amount (total or specific binding) of the bound radioactively labeled thioflavin derivative or analogue of the present invention is measured and compared (as a ratio) with the amount of labeled thioflavin derivative bound to the organ of the patient. This ratio is then compared to the same ratio in age-matched normal organ.

The amyloid imaging agents of the present invention can be administered in the form of injectable compositions, as noted above, but may also be formulated into well known drug delivery systems (e.g., oral, rectal, parenteral (intravenous, intramuscular, or subcutaneous), intracisternal, intravaginal, intraperitoneal, local (powders, ointments or drops), or as a buccal or nasal spray). A typical composition for such purpose comprises a pharmaceutically acceptable carrier. For instance, the composition may contain about 10 mg of human serum albumin and from about 0.5 to 500 micrograms of the labeled benzofuran compound per milliliter of phosphate buffer containing NaCl. Other pharmaceutically acceptable carriers include aqueous solutions, non-toxic excipients, including salts, preservatives, buffers and the like, as described, for instance, in REMINGTON'S PHARMACEUTICAL SCIENCES, 15th Ed. Easton: Mack Publishing Co. pp. 1405-1412 and 1461-1487 (1975) and THE NATIONAL FORMULARY XIV., 14th Ed. Washington: American Pharmaceutical Association (1975).

Examples of non-aqueous solvents are propylene glycol, polyethylene glycol, vegetable oil and injectable organic esters such as ethyl oleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial, anti-oxidants, chelating agents and inert gases. The pH and exact concentration of the various components the pharmaceutical composition are adjusted according to routine skills in the art. See, Goodman and Gilman's THE PHARMACOLOGICAL BASIS FOR THERAPEUTICS (7th Ed.).

The PET scanning protocol can comprise a standard whole body scan (covering from head to pelvis) completed 15-60 min after the injection of the radiopharmaceutical or a scan over a particular body area (e.g., heart, lungs, liver, kidneys). This scanning protocol is analogous to a whole body or a focused body area PET oncology scan performed with [F-18] 2-fluoro-2-deoxyglucose (FDG). That is, the amyloid-specific radiopharmaceutical is injected intravenously, time is allotted for radiotracer distribution throughout the body, radiotracer uptake in the organ(s) of interest, and clearance from the blood and other organs in which amyloid is absent, and a 20-40 min scan is performed over the whole body or over a particular body area to image amyloid-bound radiotracer. In addition, the imaging scan(s) can be used to subsequently direct biopsy sampling of the scanned tissue(s).

Generally, the dosage of the detectably labeled benzofuran compound according to formula (I) will vary depending on considerations such as age, condition, sex, and extent of disease in the patient, contraindications, if any, concomitant therapies and other variables, to be adjusted by a physician skilled in the art. Dose levels on the order of about 0.001 µg/kg/day to about 10,000 mg/kg/day of an inventive compound are useful for the inventive methods. In one embodiment, the dose level is about 0.001 µg/kg/day to about 10 µg/kg/day. In another embodiment, the dose level is about 0.01 µg/kg/day to about 1.0 µg/kg/day. In yet another embodiment, the dose level is about 0.1 mg/kg/day to about 100 mg/kg/day.

The specific dose level for any particular patient will vary depending upon various factors, including the activity and the possible toxicity of the specific compound employed; the age, body weight, general health, sex and diet of the patient; the time of administration; the rate of excretion; the drug combination; and the form of administration. Typically, in vitro dosage-effect results provide useful guidance on the proper doses for patient administration. Studies in animal models are also helpful. The considerations for determining the proper dose levels are well known in the art and within the skills of an ordinary physician.

Any known administration regimen for regulating the timing and sequence of drug delivery may be used and repeated as necessary to effect treatment in the inventive methods. The regimen may include pretreatment and/or co-administration with additional therapeutic agent(s).

In one embodiment, the compounds according to formula (I) are administered to an animal that is suspected of having or that is at risk of developing a disease, disorder or condition characterized by amyloid deposition. For example, the animal may be an elderly human.

In another embodiment, the inventive compounds bind to Aβ with a dissociation constant ($K_D$) of about 0.0001 µM to about 10.0 µM when measured by binding to synthetic Aβ peptide or AD brain tissue.

This invention further provides a pharmaceutical composition comprising:

(i) an effective amount of at least one inventive compound; and (ii) a pharmaceutically acceptable carrier.

The composition may comprise one or more additional pharmaceutically acceptable ingredient(s), including without limitation one or more wetting agent(s), buffering agent(s), suspending agent(s), lubricating agent(s), emulsifier(s), disintegrant(s), absorbent(s), preservative(s), surfactant(s), colorant(s), flavorant(s), sweetener(s) and therapeutic agent(s).

The composition can be formulated into solid, liquid, gel or suspension form for: (1) oral administration as, for example, a drench (aqueous or non-aqueous solution or suspension), tablet (for example, targeted for buccal, sublingual or systemic absorption), bolus, powder, granule, paste for application to the tongue, hard gelatin capsule, soft gelatin capsule, mouth spray, emulsion and microemulsion; (2) parenteral administration by subcutaneous, intramuscular, intravenous or epidural injection as, for example, a sterile solution, suspension or sustained-release formulation; (3) topical application as, for example, a cream, ointment, controlled-release patch or spray applied to the skin; (4) intravaginal or intrarectal administration as, for example, a pessary, cream or foam; (5) sublingual administration; (6) ocular administration; (7) transdermal administration; or (8) nasal administration.

In one embodiment, the composition can be formulated for intravenous administration and the carrier includes a fluid and/or a nutrient replenisher. In another embodiment, the composition is capable of binding specifically to amyloid in vivo, is capable of crossing the blood-brain barrier, is non-toxic at appropriate dose levels and/or has a satisfactory duration of effect. In yet another embodiment, the composition comprises about 10 mg of human serum albumin and from about 0.5 to 500 mg of the inventive compound per milliliter of phosphate buffer containing NaCl.

In addition, the present benzofuran compounds can be used in a method for determining the efficacy of therapy in the treatment of amyloidosis. The method involves the use of amyloid imaging as a surrogate marker. Surrogate markers are a special type of biomarker that may be used in place of clinical measurements as a clinical endpoint for drug approval purposes. For example, the measurement of cholesterol levels is now an accepted surrogate marker of atherosclerosis. The present invention involves the use of amyloid imaging as a surrogate marker of efficacy for anti-amyloid therapies.

The present method provides a means of evaluating success of anti-amyloid therapies. In some embodiments, the present method provides a means for evaluating clinical success of anti-amyloid therapies. In some embodiments, the method may be used to evaluate clinical success in mildly impaired subjects with few or no clinical symptoms to follow. The basic method of determining the efficacy of therapy in the treatment of amyloidosis involves:

(A) administering to a patient in need thereof an effective amount of compound of formula (I) or a pharmaceutically acceptable salt as described above:

(B) imaging said patient; then (C) administering to said patient in need thereof at least one anti-amyloid agent;

(D) subsequently administering to said patient in need thereof an effective amount of a compound of formula (I);

(E) imaging said patient; and (F) comparing levels of amyloid deposition in said patient before treatment with at least one anti-amyloid agent to levels of amyloid deposition in said patient after treatment with at least one anti-amyloid agent.

The detectable label includes any atom or moiety which can be detected using an imaging technique known to those skilled in the art. Typically, the detectable label is selected from the group consisting of $^3$H, $^{131}$I, $^{125}$I, $^{123}$I, $^{76}$Br, $^{75}$Br, $^{18}$F, $CH_2$—$CH_2$—X*, O—$CH_2$—$CH_2$—X*, $CH_2$—$CH_2$—$CH_2$—X*, O—$CH_2$—$CH_2$—$CH_2$—X* (wherein X*=$^{131}$I, $^{123}$I, $^{76}$Br, $^{75}$Br or $^{18}$F), $^{19}$F, $^{125}$I, a carbon-containing substituent selected from the group consisting of lower alkyl, $(CH_2)nOR'$, $CF_3$, $CH_2$—$CH_2$X, O—$CH_2$—$CH_2$X, $CH_2$—$CH_2$-$CH_2$X, O—$CH_2$—$CH_2$-$CH_2$X (wherein X=F, Cl, Br or I), CN, (C=O)—R', (C=O)N(R')$_2$, O(CO)R', COOR', CR'=CR'—$R_{ph}$ and $CR_2'$—$CR_2'$—$R_{ph}$ wherein at least one carbon is $^{11}$C, $^{13}$C or $^{14}$C and a chelating group (with chelated metal group) of the form W-L* or V-W-L*, wherein V is selected from the group consisting of —COO—, —CO—, —$CH_2$O— and —$CH_2$NH—; W is —$(CH_2)_n$ where n=0, 1, 2, 3, 4, or 5; and L* is:

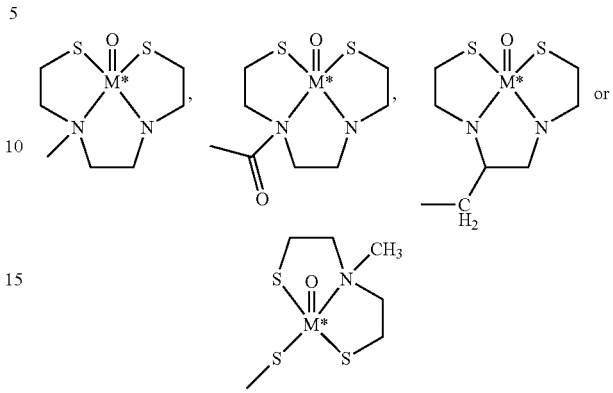

wherein M* is $^{99m}$Tc. In one embodiment, the detectable label is a radiolabel.

Anti-Amyloid Therapies and Uses

Another embodiment of the invention is a method for determining the efficacy of therapy in the treatment of amyloidosis a patient in need thereof. The method comprises administering a compound of formula (I) and then imaging the patient. After the imaging, at least one anti-amyloid agent/anti-amyloid therapy is administered to the patient. The amount administered, the route of administration, and the duration of therapy are determined by one skilled in the art based on age, weight, and condition of the patient. Such determinations are within the purview of the skilled practitioner. Suitable amounts include, but are not limited to, 0.01 to 100 mg/kg. Suitable routes of administration include, but are not limited to oral, subcutaneous and intravenous. Suitable durations of therapy include, but are not limited to one single dose to four doses per day given indefinitely. Suitable times to image include, but are not limited to immediately after the first dose to ten years after the most recent dose. Exemplary times to image include but are not limited to those between 7 days and 6 months after the most recent dose.

An "anti-amyloid agent" or an "anti-amyloid therapy" is any agent or combination of agents that treat or prevent amyloidosis. Examples of diseases associated with amyloid deposition, amyloidosis, include Alzheimer's Disease, Down's Syndrome, Type 2 diabetes mellitus, hereditary cerebral hemorrhage amyloidosis (Dutch), amyloid A (reactive), secondary amyloidosis, MCI, familial mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish)), familial amyloid cardiomyopathy (Danish), isolated cardiac amyloid, systemic senile amyloidoses, AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-I (familial amyloidotic polyneuropathy-Iowa), AApo-A-II (accelerated senescence in mice), fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele, and the condition associated with homozygosity for the apolipoprotein E4 allele or Huntington's disease. The invention contemplates diseases associated with amyloid plaque deposition. In one embodiment, the disease associated with amyloid deposition is AD.

The present benzofurans according to formula (I) can be used for amyloid imaging serving as a surrogate marker of efficacy for anti-amyloid therapy. Administration of an amyloid imaging agent to establish a baseline of amyloid deposition and subsequent imaging of a patient both before and after treatment of the patient with an anti-amyloid agent allows for determination of the efficacy of the anti-amyloid therapy. The method can be used to determine the efficacy of any anti-amyloid treatment because an amyloid imaging agent can be administered, and the patient can be imaged, before and after any anti-amyloid therapy. The method contemplates determining anti-amyloid therapies which are ineffective for treating diseases associated with amyloid deposition, as well as anti-amyloid therapies which are effective for treating diseases associated with amyloid deposition. A person of ordinary skill in the art can determine the conditions and dosing of the anti-amyloid therapy according to appropriate protocols. Therefore, the present invention contemplates determining the efficacy of anti-amyloid therapies that are now known, as well as therapies that are yet to be discovered. Exemplary non-limiting anti-amyloid therapies are described below.

In some embodiments, the efficacy of acetylcholinesterase inhibitors in the treatment of amyloidosis can be determined by the present method. Acetylcholinesterase therapy is based on studies of degeneration patterns in AD which identified substantial decreases among groups of neurons in the basal forebrain. These cells all used the transmitter acetylcholine, and their loss meant that less acetylcholine was being released at their former terminals in the cortex. Several drugs, such as tacrine, donepezil, rivastigmine and galantamine have been developed based on these findings, and are hypothesized to work by inhibiting the enzyme acetylcholinesterase (Ingram, V., *American Scientist*, 2003, 91(4):312-321).

In other embodiments, the efficacy of anti-amyloid therapy targeting enzymes responsible for formation of noxious fragments of amyloid precursor protein (APP) in the treatment of amyloidosis is determined by the inventive compounds according to the described methodology. In some embodiments, the noxious fragments of the amyloid precursor protein (APP) is misfolded $A\beta$ peptide. For example, the overproduction of $A\beta 1$-42 fragment is considered by some scientists to be a root cause of AD. The $A\beta 1$-42 fragment is formed by cleavage of APP by the $\beta$-secretase enzyme (BACE1) (which produces the amino terminus) and the $\gamma$-secretase enzyme (which cleaves the carboxyl terminus of APP). Inhibitors of these secretase enzymes may be used as anti-amyloid therapies (Ingram, V., *American Scientist*, 2003, 91(4):312-321).

In some embodiments, the efficacy of immunotherapeutic strategies in the treatment of amyloidosis can be determined by the present method. Immunotherapy works by using the patient's immune system to locate and destroy amyloid plaques and many immunotherapy strategies are being actively pursued by scientists. The immunotherapeutic strategies can be either passive or active. For example, in active immunotherapy, a patient may receive an injection or nasal-spray application of the $A\beta$ peptide, leading to an anti-amyloid immune response. Passive immunotherapy, on the other hand, might involve bypassing the beta amyloid protein, using instead antiserum that has already been produced in response to beta amyloid. Immunotherapy, involving antibodies against $A\beta$ peptide, has been studied for the treatment of AD. For example, AN-1792 is a preparation of preaggregated synthetic amyloid-beta ($A\beta$; 1-42 length) along with QS-21 adjuvant (Hock, C. et al., 2003, *Neuron*, 38:547-554). Approximately 300 AD patients have been treated with this preparation prior to suspension of the clinical trial due to side effects (Birmingham, K. and Frantz, S., 2002, *Nature Medicine*, 8:199-200).

In other embodiments, the efficacy of neuroprotective strategies in the treatment of amyloidosis is determined by the present method. For example, many clinicians recommend that patients take high doses (1000-2000 IU/day) of vitamin E. Other types of neuroprotective strategies that have been suggested for the treatment of amyloidosis are high doses of vitamin C, calcium channel modulators, free-radical scavengers, and metal ion chelators (Selkoe, et al., Annu. Rev. Pharmacol. Toxicol., 2003, 43:545-84).

In some embodiments, the efficacy of anti-inflammatory drugs (NSAIDs) strategies in the treatment of amyloidosis is determined by the present method. Treatments involving NSAIDs are based on evidence that a cellular inflammatory response in the cortex is elicited by the progressive accumulation of $A\beta$ peptide. Exemplary anti-inflammatory drugs are prednisone, nonspecific cyclooxygenase inhibitors, and cyclooxygenase-2 inhibitors. (Clark, M., et al., Annals of Internal Medicine, 2003, 138(5):400-410; and Hardy, John, Annu. Rev. Med., 2004, 55:15-25).

In some embodiments, the present method can determine the efficacy of cholesterol-lowering therapies including, but are not limited to, the 3-hydroxy-3-methylglutaryl coenzyme A reductase inhibitors (statins). Treatments involving cholesterol-lowering drugs (such as statins) are based on epidemiological evidence that patients treated with statins have a lower incidence of AD and that statins can alter the metabolism of $A\beta$ to decrease $A\beta$ levels (Wolozin, B (2002) Cholesterol and Alzheimer's disease. Biochemical Society Transactions. 30:525-529). Exemplary cholesterol-lowering statin drugs include lovastatin, pravastatin, rosuvastatin, fluvastatin, atorvastatin and simvastatin. Other cholesterol-lowering drugs include niacin, cholestyramine, fenofibrate, colesevelam and ezetimibe.

In other embodiments, the efficacy of small molecules that eliminate the neurotoxicity of the aggregated $A\beta 1$-42 in the treatment of amyloidosis is determined by the present method. Such a drug, when administered, for example, early in disease progression, would "detoxify" the gradually accumulating $A\beta$ peptide before any permanent damage is inflicted on the neurons. (Clark, M., et al., *Annals of Internal Medicine*, 2003, 138(5):400-410)

In some embodiments, the efficacy of "decoy peptides" in the treatment of amyloidosis is determined by the present method. Decoy peptides are small molecules that bind to the aggregating $A\beta 1$-42 peptide and force it to assume a nontoxic structure. Exemplary decoy peptides are small peptides (5, 6 or 9 amino acids long), selected from large libraries of protein fragments by their ability to form a tight association with tagged $A\beta 1$-42. (Clark, M., et al., *Annals of Internal Medicine*, 2003, 138(5):400-410).

In other embodiments, the efficacy of cholesterol homeostasis modulation in the treatment of amyloidosis is determined by the present method. Chronic use of cholesterol-lowering drugs has recently been associated with a lower incidence of AD. Concurrently, high-cholesterol diets have been shown to increase $A\beta$ pathology in animals, and cholesterol-lowering drugs have been shown to reduce pathology in APP transgenic mice. Clinical trials are underway to study the effect of cholesterol homeostasis modulation in the treatment of AD. (Hardy, John, Annu. Rev. Med., 2004, 55:15-25)

Certain antibodies such as the one termed m266 (DeMattos, R B, Bales, K R, Cummins, D J, Dodart, J C, Paul, S M, Holtzman, D M (2001) "Peripheral anti-A beta antibody alters CNS and plasma A beta clearance and decreases brain A beta burden in a mouse model of Alzheimer's disease" *Proc. Natl. Acad. Sci. USA* 98:8850-8855) or molecules other than antibodies (Matsuoka, Y, Saito, M, LaFrancois, J, Saito, M, Gaynor, K, Olm, V, Wang, L, Casey, E, Lu, Y, Shiratori, C, Lemere, C, Duff, K (2001) "Novel therapeutic approach for the treatment of Alzheimer's disease by peripheral administration of agents with an affinity to beta-amyloid" *Journal of Neuroscience,* 23:29-33) are believed to lower brain amyloid by binding to Aβ peptides in the blood, thereby creating a "peripheral sink" and shifting the equilibrium of Aβ from the brain to the blood, where it can be cleared from the body. Such agents are referred to herein as "peripheral sink agents."

Evaluating the Efficacy of the Anti-Amyloid Therapy

The methodology employing the benzofurans according to formula (I) for determining the efficacy of therapy in the treatment of amyloidosis comprises administering to a patient in need thereof a compound of formula (I) and imaging the patient. After imaging, at least one anti-amyloid agent is administered to the patient. Then, an effective amount of a compound of formula (I) is administered to the patient and the patient is imaged again. Finally, baseline levels of amyloid deposition in the patient before treatment with the anti-amyloid agent are compared with levels of amyloid deposition in the patient following treatment with the anti-amyloid agent. Such a comparison is within the purview of a skilled practitioner.

In some embodiments, the levels of amyloid deposition in the patient before treatment with the anti-amyloid agent will be higher than the levels of amyloid deposition in the patient following treatment with the anti-amyloid agent. Such a result indicates that the anti-amyloid agent/anti-amyloid therapy is effective in the treatment of diseases associated with amyloid deposition.

For example, AN-1792 is a preparation of preaggregated synthetic amyloid-beta (Aβ; 1-42 length) along with QS-21 adjuvant. Approximately 300 AD patients have been treated with this preparation prior to suspension of the clinical trial due to side effects (Birmingham, K. and Frantz, S., 2002, *Nature Medicine,* 8:199-200). Despite this set back, optimism over this approach has been raised by two findings. First, in the only autopsy report yet published regarding an AN-1792-treated AD patient, there were several unusual findings including: (i) extensive areas of neocortex with very few Aβ plaques; (ii) areas of cortex that were devoid of Aβ plaques contained densities of tangles, neuropil threads and cerebral amyloid angiopathy (CAA) similar to unimmunized AD, but lacked plaque-associated dystrophic neurites and astrocyte clusters; (iii) in some regions devoid of plaques, Aβ-immunoreactivity was associated with microglia (Nicoll, J. et al., 2003, *Nature Medicine* 9:448-452). Second, in a small subset of 30 AN-1792-treated patients, those patients who generated antibodies against Aβ, as determined by a tissue amyloid plaque immunoreactivity (TAPIR) assay showed significantly slower rates of decline of cognitive functions and activities of daily living, as indicated by the Mini Mental State Examination, the Disability Assessment for Dementia, and the Visual Paired Associates Test of delayed recall from the Wechsler Memory Scale, as compared to patients without such antibodies (Hock, C. et al., 2003, *Neuron,* 38:547-554).

In another embodiment, the invention contemplates administering compound according to formula (I) to patients in a method of imaging amyloid deposits in the brains of patients who do not meet clinical criteria for the diagnosis of AD. These include are but are not limited to patients presenting with clinical signs of dementia or patients with a mild cognitive impairment, such as, for example, patients presenting a dementing disorder of questionable etiology, where data from amyloid imaging of patients reveals that certain amyloid deposits are a premonitory symptom of AD or another amyloid deposition disorder.

Another embodiment of the present invention is a method of identifying a patient as prodromal to a standard clinical diagnosis of an amyloid deposition disease. The method comprises the use of amyloid imaging agents to obtain quantitative and qualitative data from a patient. Quantitative and qualitative amyloid imaging, in accordance with the present invention, should allow for earlier and more accurate diagnosis of amyloid deposit diseases, and should aid in the development of anti-amyloid therapies. The target patient for this methodology can be a patient presenting signs of clinical dementia or a patient exhibiting clinical signs of mild cognitive impairment.

In keeping with conventional practice, the practitioner may apply different criteria for a determination of signs of clinical dementia. Such criteria include but are not limited to Diagnostic and Statistical Manual of Mental Disorders, third edition (DSM-III) Alzheimer's Disease Diagnostic and Treatment Center (ADDTC), International Statistical Classification of Diseases, $10^{th}$ Revision (ICD-10), National Institute of Neurological Disorders and Stroke-Association Internationale pour la Recherche et l'Enseignment en Neurosciences (NINDS-AIREN) and Diagnostic and Statistical Manual of Mental Disorders, Fourth Edition (DSM-IV). See Pohjasvaara et al., *Stroke* 31: 2952-57 (2000).

Clinical characterization of a patient as mild cognitive impairment is well within the skill of the practitioner. The testing of a patient to elucidate such a condition involves performing a series of mental tests. The methods for clinical diagnosis are widely reviewed and are discussed, e.g., in Petersen et al., *Arch. Neurol.* 56: 303-08 (1999).

Based on clinical testing alone, subjects identified with MCI may convert to a diagnosis of AD (at a rate of about 10-15% per year), remain MCI, or revert to a diagnosis of "normal" (10-15% per year). Larrieu et al., *Neurology* 59:1594-99 (1926). Accordingly, there is considerable prognostic uncertainty associated with this clinical diagnosis. The ability to identify the presence or absence of brain amyloid deposition in a subject clinically diagnosed with MCI has the potential to greatly increase the accuracy of prognosis for conversion to AD.

The category of diseases associated with amyloid deposition includes but is not limited to Alzheimer's Disease, Down's Syndrome, Type 2 diabetes mellitus, hereditary cerebral hemorrhage amyloidosis (Dutch), amyloid A (reactive), secondary amyloidosis, familial Mediterranean fever, familial amyloid nephropathy with urticaria and deafness (Muckle-wells Syndrome), amyloid lambda L-chain or amyloid kappa L-chain (idiopathic, myeloma or macroglobulinemia-associated) A beta 2M (chronic hemodialysis), ATTR (familial amyloid polyneuropathy (Portuguese, Japanese, Swedish)), familial amyloid cardiomyopathy (Danish), isolated cardiac amyloid, systemic senile amyloidoses, AIAPP or amylin insulinoma, atrial naturetic factor (isolated atrial amyloid), procalcitonin (medullary carcinoma of the thyroid), gelsolin (familial amyloidosis (Finnish)), cystatin C (hereditary cerebral hemorrhage with amyloidosis (Icelandic)), AApo-A-I (familial amyloidotic polyneuropathy-Iowa), AApo-A-II (accelerated senescence in mice), fibrinogen-associated amyloid; and Asor or Pr P-27 (scrapie, Creutzfeld Jacob disease, Gertsmann-Straussler-Scheinker syndrome, bovine spongiform encephalitis) or in cases of persons who are homozygous for the apolipoprotein E4 allele, and the condition associated with homozygosity for the apolipoprotein E4 allele or Huntington's disease. In one embodiment, the disease associated with amyloid deposition is an amyloid plaque deposition disease. A specific disease associated with amyloid deposition is AD.

According to the invention, a basic methodology of identifying a patient as prodromal to an amyloid deposition disease entails:

(A) administering to the patient, who is presenting with signs of clinical dementia or presenting with clinical signs of a mild cognitive impairment, in need thereof an effective amount of compound of formula I described above or a pharmaceutically acceptable salt thereof;

(B) imaging said patient to obtain data and (C) analyzing said data to ascertain amyloid levels in said patient with reference to a normative patient.

One embodiment relates to a method for diagnosing a patient presenting with a dementing of questionable etiology. This method comprises determining if dementias of questionable etiology are likely to be AD or another amyloid deposition disorder based on the finding of amyloid deposition. The method comprises administering to a patient a compound of Formula (I), imaging the patient to obtain data and determining if the dementia of questionable etiology is AD based on the finding of amyloid deposition.

The term "dementing disorder of questionable etiology" refers to the condition in which a person presents for clinical evaluation (which may consist of neurological, psychiatric, medical and neuropyschological evaluations commonly employed by those skilled in the art of diagnosing persons with dementing disorders) and, after that clinical evaluation, the evaluator finds evidence that some dementing disorder may be present (based on evidence of subjective memory complaints, description of memory complaints by informants familiar with the persons deviation from normal functioning, or poor performance on neuropsychological and clinical tests commonly used by those skilled in the art), but, can not find sufficient evidence for any single clinically defined dementing disorder (such as AD, frontotemporal dementia, Dementia with Lewy Bodies, Vascular dementia, pseudodementia due to Major Depression, Creutzfeld Jacob disease and others known to those skilled in the art) or finds that the person shows evidence of more than one single dementing disorder to the degree that the distinction between these two (or more) dementing disorders is questionable in this person.

This embodiment of the invention employs amyloid imaging agents which, in conjunction with non-invasive neuroimaging techniques such as magnetic resonance spectroscopy (MRS) or imaging (MRI), or gamma imaging such as positron emission tomography (PET) or single-photon emission computed tomography (SPECT), are used to quantify amyloid deposition in vivo. These imaging techniques acquire data on many brain regions. Quantitation on specific regions is achieved by delineating "regions of interest or ROI".

In accordance with this embodiment, data obtained from patients using one of the imaging techniques mentioned above can be compared to data from normative patients with a conclusion based on criteria which distinguish the patient as prodromal to a standard clinical diagnosis of an amyloid deposition disease.

Using the same protocol, one can compare data obtained from the imaging techniques applied to the patients in order to:

define a dementing disorder of questionable etiology as being caused by an amyloid deposition disease;

distinguish Alzheimer's disease from frontotemporal dementia;

monitor a patient to determine onset of Alzheimer's disease;

diagnose Alzheimer's disease in a patient clinically diagnosed with mild cognitive impairment;

identify a patient as prodromal to Alzheimer's disease;

identify a patient as having a disease associated with an amyloid deposition disorder wherein the patient is presenting with a dementing disorder of questionable etiology or identify a patient as having Alzheimer's disease wherein the patient is presenting with a dementing disorder of questionable etiology.

Data Analysis of Amyloid Imaging

The data obtained can be quantitatively expressed in terms of Standardized Uptake Value (SUV) or in terms of pharmacokinetic modeling parameters such as the Logan distribution volume ratio (DVR) to a reference tissue such as cerebellum. Subjects who are more than one standard deviation above the typical control value of SUV or DVR would be considered to have a "positive" test and be considered to be prodromal to a clinical diagnosis of an amyloid deposition disease such as AD. Specifically, subjects can be considered "positive" if their 40-60 min average SUV is greater than 1.0 in frontal, parietal or posterior cingulate cortex. This value clearly separated AD patients from controls in the initial human study (Klunk, et al., 2004, Ann. Neurol., 55(3):306-19). Likewise, subjects can be considered "positive" if their Logan DVR value exceeds 1.5 in frontal, parietal or posterior cingulate cortex. These brain areas and exact cutoffs are given only as examples and further work may disclose additional brain areas that are useful and the cutoff values may be refined and other modeling techniques (such as compartmental modeling, graphical analysis, reference tissue modeling or spectral analysis) may be applied to determine the cutoffs. In addition, the scan data can be qualitatively interpreted from images that reflect the regional brain distribution of either SUV, Logan DVR or other parameters in which one having ordinary skill in the art of interpreting PET scans can determine that the qualitative amount and distribution of amyloid is consistent with a prodromal phase of a clinically diagnosed amyloid deposition disease.

In another embodiment of the invention, in vivo or in vitro detection is effected, in relation to a subject who has or who is at risk of having at least one amyloid deposit (i.e., a deposit comprised of at least one amyloidogenic protein), via a methodology that entails:

(a) administering to a subject suffering from a disease associated with amyloidosis, a detectable quantity of a pharmaceutical composition comprising at least one compound of formula (I) as described above and pharmaceutically acceptable salts thereof; and (b) detecting the binding of the compound to an amyloid deposit comprising at least one amyloidogenic protein, wherein the amyloidogenic protein is selected from the group consisting of AL, AH, ATTR, Aβ2M, AA, AApoAI, AApoAII, AGel, ALys, AFib, ACys, ABri, ADan, APrP, ACal, AlAPP, AANF, APro, AIns, AMed, AKer, A(tbn), and ALac.

In primary systemic amyloidosis (AL), the amyloidogenic protein can be abnormally conformed monoclonal immunoglobulin light chains (k or λ) produced by clonal plasma cells. Fibrils deposit in kidneys, heart, liver, and other organs/tissues.

In a few cases, immunoglobulin chain amyloidosis fibrils contain only heavy chain sequences rather than light chain sequences. In that circumstance, the disease is termed "heavy chain amyloidosis" (AH).

In transthyretin amyloidosis, the precursor protein is the normal or mutant sequence TTR, a transport protein synthesized in the liver and choroid plexus. TTR is a tetramer of 4 identical subunits of 127 amino acids each. Normal-sequence TTR forms amyloid deposits in the cardiac ventricles of elderly (>70 year-old) individuals; this disease is also called "senile cardiac amyloidosis." The prevalence of TTR cardiac amyloidosis increases progressively with age, affecting 25% or more of the population older than 90 years. Normal-sequence ATTR can be an incidental autopsy finding, or it can cause clinical symptoms (e.g., heart failure and arrhythmias).

Point mutations in TTR increase the tendency of TTR to form amyloid. Amyloidogenic TTR mutations are inherited as an autosomal dominant disease with variable penetrance. More than 60 amyloidogenic TTR mutations are known. The most prevalent TTR mutations are TTR Val30Met (common in Portugal, Japan, and Sweden), and TTR Val122Ile (carried by 3.9% of African Americans). Amyloidogenic TTR mutations cause deposits primarily in the peripheral nerves, heart, gastrointestinal tract, and vitreous.

In β2-microglobulin amyloidosis, the precursor protein is a normal β-microglobulin (β2M), which is the light chain component of the major histocompatibility complex. In the clinical setting, Aβ2M is associated with patients on dialysis and, rarely, patients with renal failure who are not on dialysis.

β2M is normally catabolized in the kidney. In patients with renal failure, the protein accumulates in the serum. Conventional dialysis membranes do not remove β2M; therefore, serum levels can reach as high as 30-60 times the reference range values in patients on hemodialysis. Typical organs involved include the carpal ligament and, possibly, the synovial membranes (leading to arthropathies and bone cysts) and the heart, gastrointestinal tract, liver, lungs, prostate, adrenals, and tongue.

Amyloid A (AA) amyloidosis is the most common form of systemic amyloidosis worldwide. It occurs in the course of a chronic inflammatory disease of either infectious or noninfectious etiology. In AA, the kidney, liver, and spleen are the major sites of involvement.

Apolipoprotein AI amyloidosis (AApoAI) is an autosomal dominant amyloidosis caused by point mutations in the apoAI gene. Usually, this amyloidosis is a prominent renal amyloid. Some kindreds have peripheral neuropathy or cardiac disease. ApoAI (likely of normal sequence) also is the fibril precursor in localized amyloid plaques in the aorta of elderly people.

Apolipoprotein AII amyloidosis (AApoAII) is an autosomal dominant amyloidosis caused by point mutations in the apoAII gene. The 2 kindreds described with this disorder have each carried a point mutation in the stop codon, leading to production of an abnormally long protein.

The precursor protein in gelsolin amyloidosis (AGel) is the actin-modulating protein gelsolin. Amyloid fibrils include a gelsolin fragment that contains a point mutation.

Fibrinogen amyloidosis (AFib) is an autosomal dominant amyloidosis caused by point mutations in the fibrinogen alpha chain gene.

Lysozyme amyloidosis (ALys) is an autosomal dominant amyloidosis caused by point mutations in the lysozyme gene.

The precursor protein in cystatin C amyloidosis (ACys) is cystatin C, which is a cysteine protease inhibitor that contains a point mutation. This condition is clinically termed HCHWA, Icelandic type. ACys is autosomal dominant. Clinical presentation includes multiple strokes and mental status changes beginning in the second or third decade of life. The pathogenesis is one of mutant cystatin that is widely distributed in tissues, but fibrils form only in the cerebral vessels; therefore, local conditions are believed to play a role in fibril formation.

The precursor protein in prion protein amyloidosis (APrP) is a prion protein, which is a plasma membrane glycoprotein. The etiology is either infectious (i.e., kuru) or genetic (i.e., Creutzfeldt-Jakob disease (CJD), Gerstmann-Straussler-Scheinker (GSS) syndrome, fatal familial insomnia (FFI)). The infectious unit is the prion protein, which induces a conformational change in a homologous protein encoded by a host chromosomal gene. Patients with CJD, GSS, and FFI carry autosomal dominant amyloidogenic mutations in the prion protein gene; therefore, the amyloidosis forms even in the absence of an infectious trigger.

In calcitonin amyloid (ACal), the precursor protein is calcitonin, a calcium regulatory hormone synthesized by the thyroid. Patients with medullary carcinoma of the thyroid may develop localized amyloid deposition in the tumors, consisting of normal-sequence procalcitonin (ACal). The presumed pathogenesis is increased local calcitonin production, leading to a sufficiently high local concentration of the peptide causing polymerization and fibril formation.

In islet amyloid polypeptide amyloidosis (AIAPP), the precursor protein is an islet amyloid polypeptide (IAPP), also known as amylin. IAPP is a protein secreted by the islet beta cells that are stored with insulin in the secretory granules and released in concert with insulin. Normally, IAPP modulates insulin activity in skeletal muscle. IAPP amyloid is found in insulinomas and in the pancreas of many patients with diabetes mellitus type 2.

Atrial natriuretic factor amyloidosis is associated with the precursor protein, atrial natriuretic factor (ANF), a hormone controlling salt and water homeostasis, which is synthesized by the cardiac atria. Amyloid deposits are localized to the cardiac atria. This condition is highly prevalent in elderly people. Atrial natriuretic factor amyloidosis (AANF) is most common in patients with long-standing congestive heart failure, presumably because of persistent ANF production.

In prolactin amyloid (APro), prolactin or prolactin fragments are found in the pituitary amyloid. This condition is often observed in elderly people and has also been reported in an amyloidoma in a patient with a prolactin-producing pituitary tumor.

Amyloids of the skin react with some antikeratin antibodies to generate a localized form of amyloidosis. However, the exact identity of the fibrils is not chemically confirmed in keratin amyloid, but they are referred to as keratin amyloid proteins (AKer).

Aortic medial amyloid occurs in most people older than 60 years. Medin amyloid (AMed) is derived from a proteolytic fragment of lactadherin, a glycoprotein expressed by mammary epithelium.

Familial British dementia (FBD) is characterized neuropathologically by deposition of a unique amyloid-forming protein, ABri. It is a fragment of an abnormal form of a precursor protein, BRI.

In Familial Danish dementia (FDD), a decamer duplication between codons 265 and 266 in the 3' region of the BRI gene originates an amyloid peptide named ADan, 11 residues longer than the wild-type peptide produced from the normal BRI gene. ADan deposits have been found widely distributed in the CNS of FDD cases. The deposits of ADan are predominantly non-fibrillar aggregates.

The ABri and ADan peptides are fragments derived from a larger, membrane-anchored precursor protein, termed BRI precursor protein, and encoded by the BRI gene on chromosome 13.

Pindborg tumor is characterized by the production of large amounts of amyloid and the presence of calcified lamellar bodies. The amyloid protein associated with this syndrome has yet to be named but is commonly referred to as A(tbn).

Amyloid fibrils can be formed in the absence of serum amyloid P(SAP) component and heparin sulfate proteoglycans from several natural polypeptides, such as insulin. This gives rise to the amyloid protein, AIns, the precursor of which is insulin.

Another protein, lactoferrin, is reported as the major fibril protein in familial subepithelial corneal amyloidosis. It is presumed that either a structural abnormality or abnormally increased concentration in the serum gives rise to the amyloid protein ALac.

The amyloidogenic proteins are detected by the present thioflavin compounds. The thioflavin compounds target at least one amyloidogenic protein which is derived from at least one protein precursor selected from the group consisting of immunoglobulin light chain, immunoglobulin heavy chain, transthyretin, β2-microglobulin, (Apo)serum AA, Apolipoprotien AI, Apolipoprotein AII, gelsolin, lysozyme, fibrinogen α-chain, cystatin C, ABriPP, ADanPP, prion protein, (Pro)calcitonin, islet amyloid polypeptide, atrial natriuretic factor, prolactin, insulin, lactadherin, kerato-epithelin, Pindborg tumor associated precursor protein (tbn) and lactoferrin. It is these protein targets which give rise to different syndromes or diseases of affected tissues. See Buxbaum, *Curr. Opin Rheumatol* 16: 67-75 (2003). See also, Merlini and Westermark, *J Intern Med* 255: 159-178 (2004).

The following examples are given to illustrate the present invention. It should be understood, however, that the invention is not to be limited to the specific conditions or details described in these examples.

EXAMPLES

Synthesis Examples

Example 1

Preparation of 5-Methoxy-2-(4'-fluorophenyl)benzofuran

Scheme:

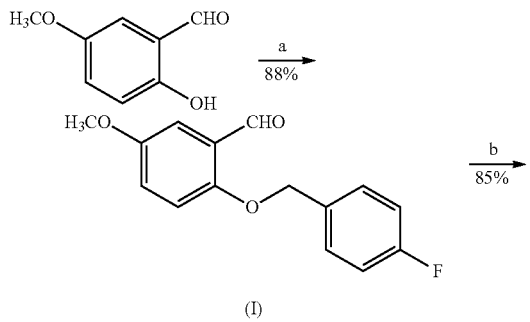

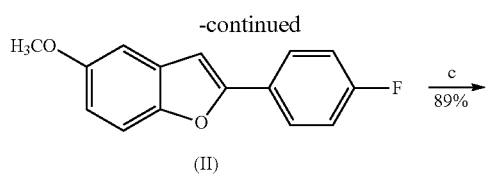

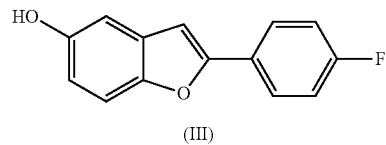

a. 4-fluorobenzylbromide, $K_2CO_3$, $CH_3CN$, refluxing 4 h;
b. $P_4$-t-Bu, Toluene, refluxing 12 h;
c. $BBr_3$, $CHCl_3$, r.t. 3 hr.

2-Benzyloxy-5-methoxybenzaldehyde (I)

To a solution of 2-hydroxy-5-methoxybenzaldehyde (0.152 g, 1.0 mmol) in dry MeCN (50 mL) was added 4-fluorobenzyl bromide (0.145 mg, 1.0 mmol), and anhydrous $K_2CO_3$ (0.27 g, 2.0 mmol). The mixture was refluxed under stirring for 4 h, and then evaporated in vacuo. Water (100 mL) was added and the mixture was extracted with EtOAc. The separated organic layer was dried with $MgSO_4$, and then evaporated in vacuum. Finally, the residue was eluted through a silica gel column with n-hexane/EtOAc (4:1) to give white compound I (0.21 g, 88%).

$^1$H NMR (300 MHz, acetone-$d_6$): δ 10.56 (s, 1H, CHO), 7.35-7.48 (m, 2H), 7.12-7.19 (m, 5H), 5.20 (s, 2H, $OCH_2$), 3.90 (s, 3H, $OCH_3$).

5-Methoxy-2-(4'-fluorophenyl)benzofuran (II)

To a solution of compound I (50 mg, 0.2 mmol) in dry toluene (5 mL) was added phosphazene base ($P_4$-t-Bu) solution in hexane (0.2 mL, 1.0 M), and refluxed overnight. $CHCl_2$ (50 mL) was added and the solution was washed with water. The separated organic layer was dried with $MgSO_4$, and then evaporated in vacuum. Finally the residue was separated through a silica gel TCL with hexane/EtOAc (4:1) to obtain white compound II (39 g, 85%).

$^1$H NMR (300 MHz, acetone-$d_6$): δ 7.92-7.98 (m, 2H), 7.46 (d, J=8.4 Hz, 1H), 7.21-7.28 (m, 3H), 7.15 (d, J=2.7 Hz, 1H), 6.90 (dd, J=3 Hz, 1H), 3.90 (s, 3H, $OCH_3$).

5-Hydroxy-1-(4'-fluorophenyl)benzofuran (III)

A solution of compound II (24 mg, 0.1 mmol) in 5 mL methylene dichloride was added to 2 mL of a 1.0 M solution of $BBr_3$ in methylene dichloride and stirred at room temperature for 3 h. The solvent was removed by evaporation, and the crude product was purified on silica gel TLC with hexane/EtOAc (3:1) to give white compound III (21 mg, 89%).

$^1$H NMR (300 MHz, acetone-$d_6$): δ 8.15 (s, 1H), 7.92-7.95 (m, 2H), 7.37 (d, J=8.7 Hz, 1H), 7.26 (t, $J_1$=$J_2$=8.9 Hz, 2H), 7.14 (s, 1H), 7.02 (d, J=2.4 Hz, 1H), 6.85 (dd, J=2.4 Hz, 1H).

Example 2

Preparation of 5-Methoxy-2-(4'-nitrophenyl)benzofuran

Scheme:

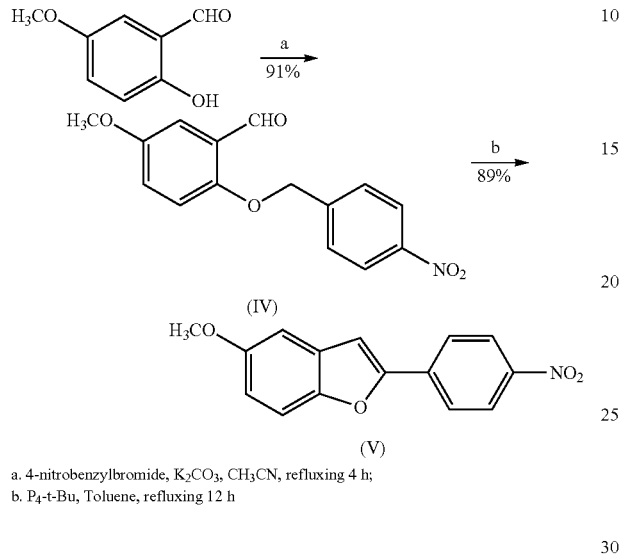

a. 4-nitrobenzylbromide, K₂CO₃, CH₃CN, refluxing 4 h;
b. P₄-t-Bu, Toluene, refluxing 12 h

3-Methoxy-2-(4'-nitrobenzyloxy)benzaldehyde (IV)

Compound IV was synthesized from 4-nitrophenyl chloride as same procedure as preparation of compound I in 91% yield.

$^1$H NMR (300 MHz, acetone-$d_6$): δ 8.36 (d, J=9.0 Hz, 2H), 8.18 (d, J=9.0 Hz, 2H), 7.26-7.29 (m, 1H), 7.21-7.26 (m, 1H), 7.01 (dd, $J_1$=2.4 Hz, $J_2$=8.4 Hz, 1H), 5.46 (s, 2H), 3.84 (s, 3H).

5-Methoxy-2-(4'-nitrophenyl)benzofuran (V)

Compound V was synthesized from compound (IV) as same procedure for Compound II in 89% yield.

$^1$H NMR (300 MHz, acetone-$d_6$): δ 8.35 (d, J=8.4 Hz, 2H), 8.15 (d, J=8.4 Hz, 2H), 7.53 (d, J=8.4 Hz, 1H), 7.56 (s, 1H), 7.21 (d, J=2.3 Hz, 1H), 7.01 (dd, $J_1$=8.4 Hz, $J_2$=2.4 Hz, 1H), 3.84 (s, 3H).

Examples 3-6

Using the procedures analogous to those described in Examples 1 and 2, the following compounds were synthesized:

Example 3

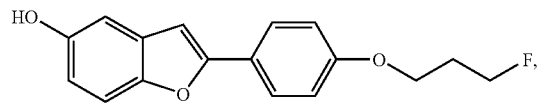

Example 4

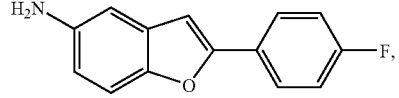

Example 5

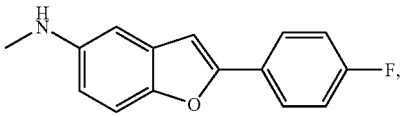

Example 6

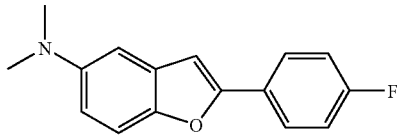

Biological Examples

Mouse Brain Entry Studies

5-Methoxy-2-(4'-fluorophenyl)benzofuran in ethanol was diluted with normal saline to make a solution containing about 500 microCuries per mL. Wild-type Swiss Webster mice were weighed, injected with approximately 30 microCuries via lateral tail vein, and killed at different times after injection. A whole blood sample was taken via cardiac puncture at the time of death, and the brain was rapidly removed and dissected into cerebellum and whole brain (no brain stem). A femur was removed from each mouse as well to determine the extent of metabolism to [$^{18}$F]fluoride. These fractions were assayed in a gamma well counter along with a calibrated portion of the injectate, and samples were decay-corrected to the time of injection. The samples were weighed, and the percent injected dose per gram tissue (% ID/g) was determined and normalized to mouse body weight ((% ID*kg)/g).

Baboon Brain Entry Studies

A 40 kg baboon was anesthetized, immobilized, and placed on a ventilator. The baboon was positioned in a PET scanner to image the brain, and a transmission scan was performed to correct for attenuation. The baboon was injected intravenously with a solution containing 8 mCi of 5-Methoxy-2-(4'-fluorophenyl)benzofuran, and the brain was imaged in a series of increasing data collection time bins over 2 h post injection. Following data acquisition, the images were reconstructed and regions of interest were drawn. Decay and attention corrected time-activity curves (TAC) were generated for each of the regions to determine the quantitative time course of radioactivity in each brain region. These TAC's indicate excellent brain penetration of the radiotracer and rapid clearance of radioactivity from normal baboon brain. These in vivo properties combined with the relatively high affinity of the ligand in vitro for aggregated amyloid indicate that the compound is a potentially useful amyloid imaging agent.

Characterization of Binding Affinity to Aβ Synthetic Peptide

The characteristics of benzofuran derivative binding were analyzed using synthetic Aβ(1-40) and 2-(4'-[$^3$H]methylamino-phenyl)-benzothiazole ([$^3$H]BTA-1) in phosphate-buffered saline (pH 7.4), as previously described. Klunk et al., Life Sci. 69:1471 (2001); Mathis et al., Bioorg. Med. Chem. Lett., 12:295 (2002). The table below lists the inhibition constants (Ki) of the four compounds shown for competition of [$^3$H]BTA-1 binding from synthetic Aβ(1-40). Compounds with Ki values below 20 nM are exemplary for use as in vivo PET radiotracers.

| Benzofurans | Ki (nM) |
|---|---|
| H$_3$CO-benzofuran-phenyl-F (Compound V) | 3.7 |
| HO-benzofuran-phenyl-F (Compound III) | 27.7 |
| H$_3$CO-benzofuran-phenyl-F | 3.9 |
| HO-benzofuran-phenyl-F | 96 |
| HO-benzofuran-phenyl-O-(CH$_2$)$_3$-F | 1.2 |
| H$_2$N-benzofuran-phenyl-F | 28 |
| MeHN-benzofuran-phenyl-F | 2.8 |
| Me$_2$N-benzofuran-phenyl-F | 2 |

What is claimed is:

1. An amyloid binding compound of Formula (I) or a pharmaceutically acceptable salt thereof:

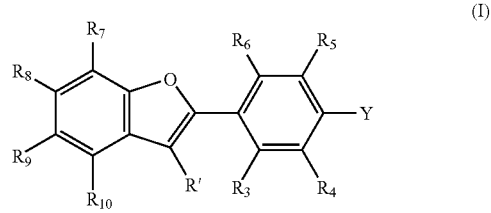

(I)

wherein
Y is H, NO$_2$, F, Cl, Br, I, O—(CR"$_2$)$_n$—X, or —(CR"$_2$)$_n$-X;
wherein
X is F, Cl, Br or I; and
n is 1-5;
R' is H or a lower alkyl group;
R" is H or a lower alkyl group;
R$_3$-R$_{10}$ are independently selected from the group consisting of H, F, Cl, Br, I, C$_1$-C$_5$ alkyl, (CH$_2$)$_{1-3}$—OR$_{11}$, CF$_3$, —(CH$_2$)$_{1-3}$—X, —O—(CH$_2$)$_{1-3}$—X, CN, —CO—R$_{11}$, —N(R$_{11}$)$_2$, —NR"$_3$$^+$, —NO$_2$, —CO—N(R$_{11}$)$_2$, —O—(CO)—R$_{11}$, OR$_{11}$, SR$_{11}$, COOR$_{11}$, R$_{ph}$, —CR$_{11}$=CR$_{11}$—R$_{ph}$ and —C(R$_{11}$)$_2$—C(R$_{11}$)$_2$—R$_{ph}$, wherein one or both of R$_8$ and R$_9$ are independently OR$_{11}$,
and wherein
X is F, Cl, Br or I; and
R$_{ph}$ is phenyl optionally substituted with one or more substituents selected from the group consisting of F, Cl, Br, I, C$_1$-C$_5$ alkyl, (CH$_2$)$_{1-3}$-OR$_{11}$, CF$_3$, —(CH$_2$)$_{1-3}$—X, —O —(CH$_2$)$_{1-3}$—X, CN, —CO—R$_{11}$, —N(R$_{11}$)$_2$, —CO—N(R$_{11}$)$_2$, —O—(CO)—R$_{11}$, OR$_{11}$, SR$_{11}$, and COOR$_{11}$, wherein each R$_{11}$ is independently H or C$_1$-C$_5$ alkyl; and
Y or R$^3$-R$^{10}$ comprises at least one detectable label selected from the group consisting of $^{131}$I, $^{123}$I, $^{124}$I, $^{125}$I, $^{76}$Br, $^{75}$Br, $^{18}$F, $^{19}$F, $^{11}$C, $^{13}$C, $^{14}$C and $^3$H.

2. The amyloid binding compound according to claim 1, wherein Y is H, F, Cl, Br, I, or —(CR"$_2$)$_n$—X, and Y comprises at least one detectable label selected from the group consisting of $^{131}$I, $^{123}$I, $^{124}$I, $^{125}$I, $^{76}$Br, $^{75}$Br, $^{18}$F, $^{19}$F, $^{11}$C, $^{13}$C, $^{14}$C and $^3$H.

3. The amyloid binding compound according to claim 2, wherein R$_3$-R$_{10}$ are independently selected from the group consisting of H, F, Cl, Br, I, —N(R$_{11}$)$_2$, and OR$_{11}$.

4. The amyloid binding compound according to claim 3, wherein each of R$_7$ and R$_{10}$ is H.

5. The amyloid binding compound according to claim 4, wherein each of R$_3$, R$_4$, R$_5$, and R$_6$ is H.

6. The amyloid binding compound according to claim 2, wherein Y is selected from $^{131}$I, $^{123}$I, $^{124}$I, $^{125}$I, $^{76}$Br, $^{75}$Br, $^{18}$F, $^{19}$F and $^{11}$C.

7. The amyloid binding compound according to claim 6, wherein Y is $^{11}$C or $^{18}$F.

8. The amyloid binding compound according to claim 2 having the following formula:

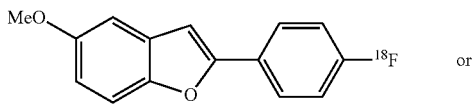

or

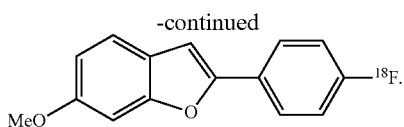

9. The amyloid binding compound according to claim 2 having the following formula:

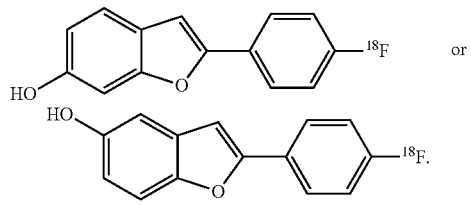

10. A pharmaceutical composition comprising
    (i) an effective amount of an amyloid binding compound according to claim 1; and
    (ii) a pharmaceutically acceptable carrier.

11. A method for detecting amyloid deposit(s) in vivo, comprising:
    (i) administering to a mammal an effective amount of an amyloid binding compound according to claim 1, wherein the compound would bind any amyloid deposit(s) in the mammal; and
    (ii) detecting binding of the compound to amyloid deposit(s) in the mammal.

12. The method according to claim 11, wherein the amyloid deposit(s) is/are located in the brain of the mammal.

13. The method according to claim 11, wherein the mammal is a human who is suspected of having Alzheimer's disease, familial Alzheimer's disease, Down's syndrome or homozygotes for apolipoprotein E4 allele.

14. The method according to claim 11, wherein the detecting is effected by gamma imaging, magnetic resonance imaging or magnetic resonance spectroscopy.

15. The method according to claim 14, wherein the detecting is effected by gamma imaging.

16. The method according to claim 15, wherein the gamma imaging is PET or SPECT.

17. The method according to claim 11, wherein the compound is administered intravenously.

18. A method for detecting amyloid deposit(s) in vitro comprising:
    (i) contacting a bodily tissue with an effective amount of an amyloid binding compound according to claim 1, wherein the compound would bind any amyloid deposit(s) in the tissue; and
    (ii) detecting binding of the compound to amyloid deposit(s) in the tissue.

19. The method according to claim 18, wherein the compound is in a solution that further comprises 25-99% ethanol, with the remainder of the solution being water.

20. The method according to claim 18, wherein the solution comprises 0-50% ethanol and 0.0001 to 100 µM of the compound.

21. The method according to claim 18, wherein the detecting is effected by bright-field, fluorescence, laser-confocal or cross-polarization microscopy.

22. The method according to claim 18, wherein the method further comprises:
    (iii) separating from the tissue the amyloid deposit(s) bound to the compound; and
    (iv) quantifying the amyloid deposit(s) bound to the compound.

23. A method for distinguishing an Alzheimer's diseased brain from a normal brain comprising:
    (i) obtaining tissues from (i) the cerebellum and (ii) another area of the same brain, of a normal mammal and of a mammal suspected of having Alzheimer's disease;
    (ii) contacting the tissues with an amyloid binding compound according to claim 1;
    (iii) quantifying the amyloid bound to the compound;
    (iv) calculating the ratio of (a) the amount of amyloid in the area of the brain other than the cerebellum to (b) the amount of amyloid in the cerebellum; and
    (v) comparing the ratio for a normal mammal with the ratio for a mammal suspected of having Alzheimer's disease.

24. The method according to claim 23, wherein the ratio of (i) binding of the compound to a brain area other than the cerebellum to (ii) binding of the compound to the cerebellum, in the subject, is compared to the ratio in normal subjects.

25. A method of detecting amyloid deposits in biopsy or post-mortem human or animal tissue comprising the steps of:
    (a) incubating formalin-fixed or fresh-frozen tissue with a solution of an amyloid binding compound of claim 1 or a pharmaceutically acceptable salt thereof to form a labeled deposit; and
    (b) detecting the labeled deposit.

26. The method according to claim 25 wherein the solution is composed of 25-100% ethanol, with the remainder of the solution being water, wherein the solution is saturated with the compound of formula (I).

27. The method according to claim 25 wherein the solution is composed of an aqueous buffer containing 0-50% ethanol, wherein the solution contains 0.0001 to 100 µM of the compound of formula (I).

28. The method according to claim 25 wherein the detecting is effected by microscopic techniques selected from the group consisting of bright-field, fluorescence, laser-confocal, and cross-polarization microscopy.

29. A method of quantifying the amount of amyloid in biopsy or post-mortem tissue comprising the steps of:
    a) incubating a radiolabeled derivative of an amyloid binding compound of claim 1 or a pharmaceutically acceptable salt thereof with a homogenate of biopsy or post-mortem tissue, wherein at least one of the substituents in the compound is labeled with a radiolabel selected from the group consisting of $^{125}I$, $^{3}H$, and a carbon-containing substituent, wherein at least one carbon is $^{14}C$;
    b) separating the tissue-bound from the tissue-unbound radiolabeled compound of claim 1,
    c) quantifying the tissue-bound radiolabeled compound of claim 1, and
    d) converting the units of tissue-bound radiolabeled compound of claim 1 to units of micrograms of amyloid per 100 mg of tissue by comparison with a standard.

30. A method of selectively binding an amyloid binding compound of claim 1 or a pharmaceutically acceptable salt thereof to amyloid plaques but not neurofibrillary tangles in brain tissue which contains both, the method comprising contacting the amyloid plaques in in vitro binding or staining assays with a compound of claim 1 at a concentration below about 10 nM.

31. A method of selectively binding in vivo an amyloid binding compound of Formula (I) or a pharmaceutically acceptable salt thereof to amyloid plaques but not to neurofibrillary tangles in brain tissue which contains both, the method comprising administering an effective amount of a compound of claim 1 or a pharmaceutically acceptable salt thereof such that the blood concentration of the administered compound remains below about 10 nM in vivo.

32. An in vivo or in vitro method for detecting in a subject at least one amyloid deposit comprising at least one amyloidogenic protein, comprising the steps of:
   (a) administering to a subject suffering from a disease associated with amyloidosis, a detectable quantity of a pharmaceutical composition comprising at least one amyloid binding compound of claim 1 or a pharmaceutically acceptable salt thereof and a pharmaceutically acceptable carrier, and
   (b) detecting the binding of the compound to an amyloid deposit comprising at least one amyloidogenic protein.

33. The method according to claim 32, wherein the subject is suffering from a disease associated with systemic amyloidosis.

34. The method according to claim 33, wherein the at least one amyloid deposit is located in a mesodermal tissue of the subject.

35. The method according to claim 34, wherein the tissue is selected from the group consisting of peripheral nerve, skin, tongue, joint, heart or liver.

36. The method according to claim 33, wherein the at least one amyloid deposit is located in a parenchymatous organ.

37. The method according to claim 36, wherein the organ is selected from the group consisting of spleen, kidney, liver and adrenal.

38. The method according to claim 33, wherein the disease associated with systemic amyloidosis is selected from the group consisting of multiple myeloma, macroglobulinemia, lymphoma, chronic inflammatory disease, rheumatoid arthritis, infectious disease, dermatomyositis, scleroderma, regional enteritis, ulcerative colitis, tuberculosis, chronic osteomyelitis, bronchiectasis, skin abscess, lung abscess, cancer, Hodgkin's disease, heredofamilial amyloidosis, familial Mediterranean fever, familial dementia and familial amyloid polyneuropathy.

39. The method according to claim 38, where said skin or lung abscess results from subcutaneous heroin use.

40. The method according to claim 32, wherein the detecting is selected from the group consisting of gamma imaging, magnetic resonance imaging and magnetic resonance spectroscopy.

41. The method according to claim 40, wherein the detecting is done by gamma imaging, and the gamma imaging is either PET or SPECT.

42. The method according to claim 32, wherein the pharmaceutical composition is administered by intravenous injection.

43. The method according to claim 32, wherein the subject is receiving hemodialysis for chronic renal failure.

44. The method according to claim 32, wherein the subject is suffering from a disease associated with localized amyloidosis.

45. The method according to claim 44, wherein the at least one amyloid deposit is located in a tissue selected from the group consisting of tenosynovium, joints, aortic, thyroid, islets of langerhans, aging pituitary, Iatrogenic, cardiac atria, and cornea.

46. The method according to claim 44, wherein the at least one amyloid deposit is located in the pancreas.

47. The method according to claim 44, wherein the disease associated with localized amyloidosis is selected from the group consisting of primary myeloma, familial dementia, spongioform encephalopathies, c-cell thyroid tumor, insulinoma, prolactinoma and pindborg tumor.

48. A method of identifying a patient as prodromal to a disease associated with amyloid deposition comprising:
   (A) administering to the patient, who is presenting with signs of clinical dementia or clinical signs of a mild cognitive impairment, an amyloid binding compound of formula (I) claim 1 or a pharmaceutically acceptable salt thereof;
   then
   (B) imaging said patient to obtain data;
   and
   (C) analyzing said data to ascertain amyloid levels in said patient with reference to a normative level, thereby identifying said patient as prodromal to a disease associated with amyloid deposition.

49. The method according to claim 48, wherein the patient is diagnosed with mild cognitive impairment.

50. The method according to claim 48, wherein the amyloid disease is Alzheimer's disease.

51. The method according to claim 48, wherein the imaging is selected from the group consisting of gamma imaging, magnetic resonance imaging and magnetic resonance spectroscopy.

52. The method according to claim 51, wherein the imaging is done by gamma imaging, and the gamma imaging is PET or SPECT.

53. The method according to claim 48, where said data define a dementing disorder of questionable etiology as being caused by an amyloid deposition disease.

54. The method according to claim 53, comprising distinguishing Alzheimer's disease from frontotemporal dementia.

55. The method according to claim 49, further comprising monitoring said patient to determine onset of Alzheimer's disease.

56. The method according to claim 48, which comprises diagnosing Alzheimer's disease in a patient clinically diagnosed with mild cognitive impairment.

57. The method according to claim 48, wherein the disease associated with amyloid deposition is Alzheimer's disease.

58. The method according to claim 48, wherein the patient is presenting with a dementing disorder of questionable etiology.

59. The method according to claim 58, wherein the patient has undiagnosed AD.

60. The method according to claim 48, wherein the patient has undiagnosed AD.

61. A method of determining the efficacy of therapy in the treatment of amyloidosis, comprising:
   (A) administering to a patient in need thereof an effective amount of an amyloid binding compound of claim 1 or a pharmaceutically acceptable salt thereof;
   (B) imaging said patient; then
   (C) administering to said patient in need thereof at least one anti-amyloid agent;
   (D) subsequently administering to said patient in need thereof an effective amount of a compound of claim 1;
   (E) imaging said patient; and
   (F) comparing levels of amyloid deposition in said patient before treatment with said at least one anti-amyloid agent to levels of amyloid deposition in said patient after treatment with said at least one anti-amyloid agent.

62. The method according to claim 61, wherein the agent comprises one or more antibodies against Aβ peptide.

63. The method according to claim 61, wherein the agent comprises one or more inhibitors of β- and/or γ-secretase.

64. The method according to claim 61, wherein the agent comprises a small molecule that binds to Aβ1-42.

65. The method according to claim 64, wherein the agent is a decoy peptide.

66. The method according to claim 61, wherein said amyloidosis is AD.

67. The method according to claim 61, wherein the imaging is selected from the group consisting of gamma imaging, magnetic resonance imaging, and magnetic resonance spectroscopy.

68. The method according to claim 67, wherein the imaging is done by gamma imaging, and the gamma imaging is PET or SPECT.

69. The method according to claim 64, wherein the agent is a peripheral sink agent.

* * * * *

UNITED STATES PATENT AND TRADEMARK OFFICE
CERTIFICATE OF CORRECTION

| | | Page 1 of 1 |
|---|---|---|
| PATENT NO. | : 8,138,360 B2 | |
| APPLICATION NO. | : 12/064146 | |
| DATED | : March 20, 2012 | |
| INVENTOR(S) | : William E. Klunk and Chester A. Mathis, Jr. | |

It is certified that error appears in the above-identified patent and that said Letters Patent is hereby corrected as shown below:

In the Specifications:

Please add the following paragraph column 1 after the title and before the Field of the Invention:

This invention was made with government support under grant number AG018402 awarded by the National Institutes of Health. The government has certain rights in the invention.

Signed and Sealed this
Third Day of July, 2012

David J. Kappos
*Director of the United States Patent and Trademark Office*